(12) United States Patent
Kaye et al.

(10) Patent No.: US 8,963,082 B2
(45) Date of Patent: Feb. 24, 2015

(54) MINIATURIZED ION MOBILITY SPECTROMETER

(75) Inventors: William J. Kaye, Lake Worth, FL (US); Robert M. Stimac, Palm Beach Gardens, FL (US)

(73) Assignee: Rapiscan Systems, Inc., Torrance, CA (US)

( * ) Notice: Subject to any disclaimer, the term of this patent is extended or adjusted under 35 U.S.C. 154(b) by 978 days.

(21) Appl. No.: 11/760,388

(22) Filed: Jun. 8, 2007

(65) Prior Publication Data

US 2009/0032695 A1 Feb. 5, 2009

Related U.S. Application Data

(60) Provisional application No. 60/812,463, filed on Jun. 9, 2006.

(51) Int. Cl.
*H01J 49/00* (2006.01)
*G01N 27/62* (2006.01)

(52) U.S. Cl.
CPC .............. *H01J 49/00* (2013.01); *G01N 27/622* (2013.01)
USPC ............................ 250/290; 250/281; 250/282

(58) Field of Classification Search
None
See application file for complete search history.

(56) References Cited

U.S. PATENT DOCUMENTS

| 3,593,018 A | 7/1971 | Cohen |
| 3,621,239 A | 11/1971 | Cohen |
| 3,621,240 A | 11/1971 | Cohen et al. |
| 3,624,389 A | 11/1971 | Cohen et al. |
| 3,626,178 A | 12/1971 | Cohen |
| 3,626,179 A | 12/1971 | Cohen |
| 3,626,180 A | 12/1971 | Carroll et al. |
| 3,626,181 A | 12/1971 | Wernlund |
| 3,626,182 A | 12/1971 | Cohen |
| 3,629,574 A | 12/1971 | Carroll |
| 3,668,382 A | 6/1972 | Cohen et al. |
| 3,668,383 A | 6/1972 | Carroll |
| 3,668,385 A | 6/1972 | Cohen |
| 3,697,748 A | 10/1972 | Cohen |
| 3,697,749 A | 10/1972 | Wernlund |
| 3,699,333 A | 10/1972 | Cohen et al. |
| 3,845,301 A | 10/1974 | Wernlund et al. |
| 4,105,746 A * | 8/1978 | Compton et al. ............. 423/251 |
| 4,311,669 A * | 1/1982 | Spangler ........................ 422/98 |
| 4,390,784 A * | 6/1983 | Browning et al. ............ 250/287 |
| 4,839,143 A * | 6/1989 | Vora et al. ....................... 422/98 |
| 4,849,903 A * | 7/1989 | Fletcher et al. ................. 702/65 |
| 4,855,595 A | 8/1989 | Blanchard |
| 5,053,343 A * | 10/1991 | Vora et al. ..................... 436/153 |
| 5,162,652 A | 11/1992 | Cohen et al. |
| 5,175,431 A * | 12/1992 | Eisele et al. .................. 250/288 |

(Continued)

OTHER PUBLICATIONS

W. Blanchard et al,"Ion Injection in a Mobility Spectrometer Using Field Gradient Barriers, i.e. Ion Wells", IJIMS 5, 3:15-18 (2002).

*Primary Examiner* — Andrew Smyth
(74) *Attorney, Agent, or Firm* — Novel IP

(57) ABSTRACT

By utilizing the combination of a unique electronic ion injection control circuit in conjunction with a particularly designed drift cell construction, the instantly disclosed ion mobility spectrometer achieves increased levels of sensitivity, while achieving significant reductions in size and weight. The instant IMS is of a much simpler and easy to manufacture design, rugged and hermetically sealed, capable of operation at high temperatures to at least 250° C., and is uniquely sensitive, particularly to explosive chemicals.

23 Claims, 19 Drawing Sheets

(56) References Cited

U.S. PATENT DOCUMENTS

| | | | |
|---|---|---|---|
| 5,200,614 A | 4/1993 | Jenkins | |
| 5,206,506 A * | 4/1993 | Kirchner | 250/281 |
| 5,218,203 A * | 6/1993 | Eisele et al. | 250/288 |
| 5,294,794 A * | 3/1994 | Davies | 250/287 |
| 5,345,809 A * | 9/1994 | Corrigan et al. | 73/23.2 |
| 5,373,157 A * | 12/1994 | Hiroki et al. | 250/292 |
| 5,412,200 A * | 5/1995 | Rhoads | 250/201.9 |
| 5,448,053 A * | 9/1995 | Rhoads | 250/201.9 |
| 5,455,417 A * | 10/1995 | Sacristan | 250/287 |
| 5,457,316 A | 10/1995 | Cohen et al. | |
| 5,465,607 A * | 11/1995 | Corrigan et al. | 73/23.36 |
| 5,485,277 A * | 1/1996 | Foster | 356/445 |
| 5,585,575 A * | 12/1996 | Corrigan et al. | 73/863.71 |
| 5,789,745 A * | 8/1998 | Martin et al. | 250/286 |
| 5,905,258 A * | 5/1999 | Clemmer et al. | 250/287 |
| 5,965,882 A * | 10/1999 | Megerle et al. | 250/287 |
| 6,084,227 A * | 7/2000 | Rhoads | 250/201.9 |
| 6,344,640 B1 * | 2/2002 | Rhoads | 250/201.9 |
| 6,429,415 B1 * | 8/2002 | Rhoads | 250/208.1 |
| 6,462,334 B1 * | 10/2002 | Little et al. | 250/281 |
| 6,606,899 B1 | 8/2003 | Ketkar et al. | |
| 6,740,873 B2 | 5/2004 | Pusterla et al. | |
| 6,828,795 B2 | 12/2004 | Krasnobaev et al. | |
| 6,895,339 B2 | 5/2005 | Pusterla et al. | |
| 6,924,479 B2 * | 8/2005 | Blanchard | 250/287 |
| 6,981,947 B2 * | 1/2006 | Melker | 600/532 |
| 7,041,508 B2 * | 5/2006 | Smith | 436/104 |
| 7,381,944 B2 * | 6/2008 | Cameron et al. | 250/282 |
| 7,714,284 B2 * | 5/2010 | Miller et al. | 250/295 |
| 2002/0014586 A1 * | 2/2002 | Clemmer | 250/287 |
| 2002/0079425 A1 * | 6/2002 | Rhoads | 250/201.9 |
| 2002/0134932 A1 * | 9/2002 | Guevremont et al. | 250/281 |
| 2003/0176804 A1 * | 9/2003 | Melker | 600/532 |
| 2003/0193338 A1 | 10/2003 | Krasnobaev et al. | |
| 2004/0094702 A1 * | 5/2004 | Clemmer | 250/283 |
| 2005/0029443 A1 * | 2/2005 | Miller et al. | 250/281 |
| 2005/0109930 A1 * | 5/2005 | Hill et al. | 250/286 |
| 2005/0253061 A1 * | 11/2005 | Cameron et al. | 250/287 |
| 2006/0054809 A1 * | 3/2006 | Giannantonio et al. | 250/292 |
| 2006/0062734 A1 * | 3/2006 | Melker et al. | 424/10.1 |
| 2006/0102835 A1 * | 5/2006 | Laser | 250/282 |
| 2007/0167853 A1 * | 7/2007 | Melker et al. | 600/532 |
| 2007/0278396 A1 * | 12/2007 | Wu | 250/282 |
| 2008/0059226 A1 * | 3/2008 | Melker et al. | 705/2 |
| 2008/0073514 A1 | 3/2008 | Landgraf et al. | |

* cited by examiner

GUARD RING STAMPED PART

SOURCE CERAMIC ISOLATOR - TYPICAL DIMENSIONS

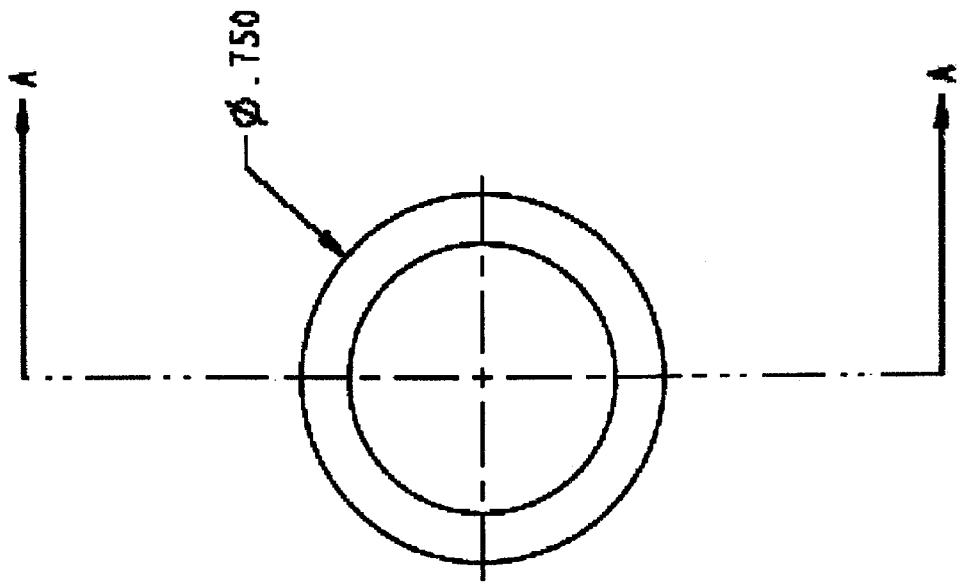
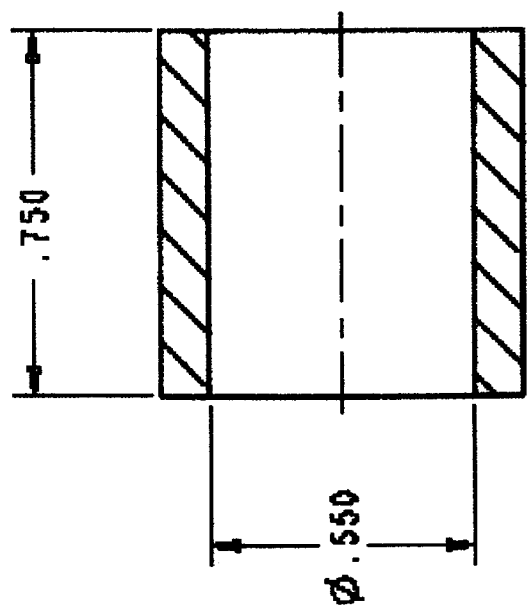
FIGURE 14C

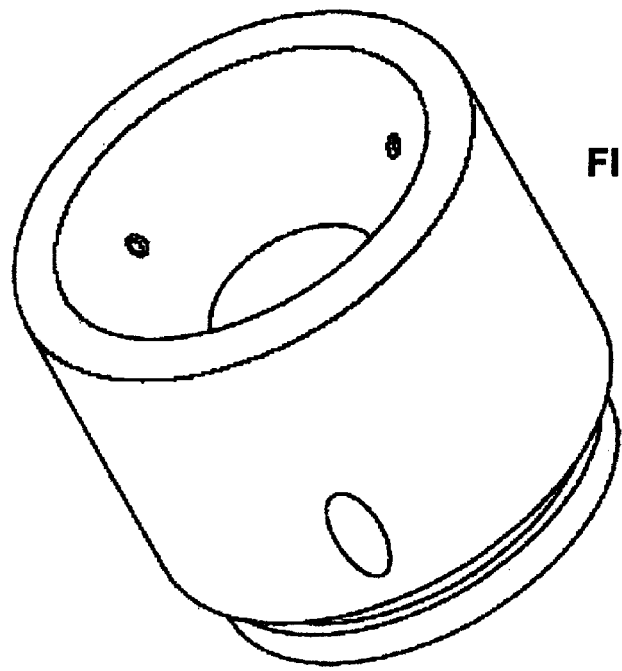
FIGURE 14D
FIGURE 14E
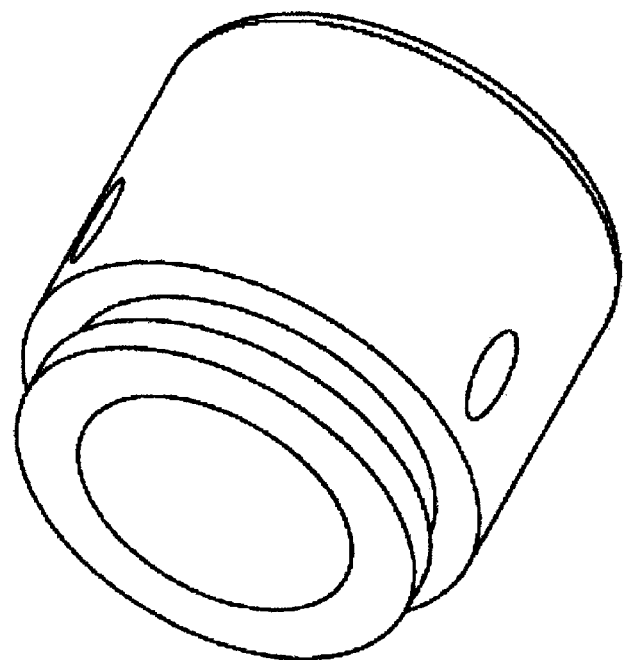

MINIATURIZED ION MOBILITY SPECTROMETER

REFERENCE TO RELATED APPLICATIONS

This application claims benefit of the filing date of U.S. Provisional Patent Application No. 60/812,463, filed on Jun. 9, 2006, the contents of which are herein incorporated by reference.

Certain aspects of this invention were made with Government support under contract numbers NAS2-03137 and NNA04CA08C awarded by NASA. The Government has certain rights in those aspects of the invention.

FIELD OF THE INVENTION

This invention relates to ion mobility spectrometry; particularly to ion mobility spectrometers having enhanced sensitivity and performance for the detection of trace chemicals; and most particularly to a highly sensitive and miniaturized Ion Mobility Spectrometer (IMS) incorporating a plurality of mechanical and electrical innovations, resulting in synergistic operability enhancements.

BACKGROUND OF THE INVENTION

The Ion Mobility Spectrometer was invented by Dr. Martin J. Cohen and others in the late 1960's at Franklin GNO Corporation in West Palm Beach. The genesis of this idea resulted from Dr. Cohen's interest in gaseous electronics and radiation physics. The original patent for IMS, U.S. Pat. No. 3,699,333 was filed in October 1968, and granted Oct. 17, 1972. This patent discloses the concept of "Plasma Chromatography", an early name for IMS and describes the instrument concept and shows a spectrum. This patent was followed by a number of others that describe refinements and expansions of the original IMS concept and instrument design, and discuss a variety of applications and analytical methodologies. These patents, all assigned to Franklin GNO, are: U.S. Pat. Nos. 3,593,018; 3,621,239; 3,621,240; 3,624,389; 3,626,178; 3,626,179; 3,626,180; 3,626,181; 3,626,182; 3,629,574; 3,668,382; 3,668,383; 3,668,385; 3,697,748; and 3,697,749. U.S. Pat. No. 3,845,301 granted Oct. 29, 1974, describes the design and functioning of an IMS very similar to those used to the current day, with the exception of the specific method of detecting and observing the ion peaks.

IMS has military and anti-terror utilities for the detection of chemical warfare (CW) agents and explosives, for which the instantly disclosed device is uniquely capable. The US and UK governments have purchased instruments for use in the area of CW agent detection, in particular.

Under government supported contract research, primarily for the FAA for explosives detection, and for NASA for a unique methodology using IMS for planetary atmosphere analyses, basic technology currently used at airports for trace vapor detection of concealed explosives was developed. The NASA work produced instrumentation that was capable of providing trace component analysis of the atmospheres of Mars, Titan, and comets. This methodology was commercialized for the analysis of ultra-high purity gases for the semiconductor industry.

Patents for an explosive detection application and for the pure gas analysis application were issued: U.S. Pat. No. 5,162,652 granted Nov. 10, 1992, and U.S. Pat. No. 5,457,316 granted Oct. 10, 1995. A number of pure gas analysis patents, both US and international, have been issued, e.g. U.S. Pat. No. 6,740,873 issued May 25, 2004, and U.S. Pat. No. 6,895,339 issued May 17, 2005.

The instant inventors have targeted commercial and government applications that require a rugged, dependable, miniature Ion Mobility Spectrometer. The initial objective was to concentrate on the explosive detection market which provides the greatest opportunity for the instantly disclosed unique miniaturized IMS. The instant inventors developed a handheld detector for trace explosives detection. However, the focus of the NASA SBIR was to continue the application of IMS for planetary atmosphere analysis in which the rugged hermetically sealed miniaturized design was important to reduce weight and consumables usage. Out of this work, another important prototype commercial application for pure gas analysis has also been developed.

DESCRIPTION OF THE PRIOR ART

U.S. Pat. No. 3,593,018, issued to Cohen on Jul. 13, 1971 is directed towards an apparatus and method for sorting and detecting ions in a drift cell, the electric fields applied to the cell being controlled at appropriate times to minimize dispersion of bunched ions produced by a pulsed source. Bunched product ions produced by ion-molecule reactions are analyzed in accordance with their velocity in a drift field.

U.S. Pat. No. 3,621,239, issued to Cohen on Nov. 16, 1971 deals with methods for sorting and detecting trace gases which undergo ion-molecule reactions. Particular species of reactant ions are selected by choice of reagent gas and/or by reactant ion filtering to produce predictable product ions by reaction with trace gas molecules of a sample. The sample may be reacted with different species of reactant ions and the results compared to confirm the presence of particular species of product ions. The reagents producing different species of reactant ions may have ionization potentials above and below the ionization potential of the expected trace gas molecules.

U.S. Pat. No. 3,624,389 issued to Cohen et al. on Nov. 30, 1971, is directed toward an apparatus and methods for sorting and detecting trace gases which undergo ion-molecule reactions. Positive or negative ions of the trace gas are formed by ion-molecule reactions between the molecules of the trace gas and primary ions from another gas. Ions are classified in accordance with their velocity in a stream of gas while subjected to an electric drift field.

U.S. Pat. No. 3,626,180 issued to Carroll et al. on Dec. 7, 1971, is directed towards apparatus and methods for sorting and detecting trace gases which undergo ion-molecule reactions, trace ions being formed in a reactive gaseous medium and being analyzed in a nonreactive gaseous medium. The ions are classified in accordance with their velocity in an electric drift field.

U.S. Pat. No. 3,626,182 issued to Cohen on Dec. 7, 1971, and is directed towards an apparatus and method for sorting and detecting ions in a drift cell, the electric fields applied to different regions of the cell being controlled at appropriate times to ensure the rapid withdrawal of the ions from a reaction region to an analysis region, the bunching of the ions in the analysis region, and thereafter the separation of the bunched ions in accordance with ion drift velocity, and detection of separated ion species.

U.S. Pat. No. 3,629,574 issued to Carroll on Dec. 21, 1971, deals with a process wherein electrons are separated from ions by subjecting these charged particles to a drift field to cause them to move from a first region toward a second region and by interposing an electron filter in the drift field between said regions, the filter comprising a pair of grid members to which high-frequency alternating voltages are applied. This principle is applied to an electron capture detector and to a device which separates and detects ions in accordance with their mobility.

U.S. Pat. No. 3,697,748 issued to Cohen on Oct. 10, 1972 is directed toward a process wherein response time of drift-cell apparatus for measuring trace gases is improved by heating the drift cell walls and/or the sample inlet to reduce the accumulation of sample substances. Heated filters and electrode structures with tortuous gas paths are also disclosed.

U.S. Pat. No. 3,697,749 issued to Wernlund on Oct. 10, 1972, is directed toward detection of small-source plumes, as by an airborne instrument, wherein ions formed from the molecules of a gaseous sample and collected by the airborne instrument are segregated in a drift field, and signals produced in response to the detection of the segregated ions are separated into short-duration plume signal components and long-duration background components. The short-duration components are indicated with enhanced resolution.

U.S. Pat. No. 3,699,333 issued to Cohen et al. on Oct. 17, 1972, is directed towards an apparatus and method for sorting and detecting trace gases which undergo ion-molecule reactions. Positive or negative ions of the trace gas are formed by ion-molecule reactions between the molecules of the trace gas and primary ions from another source. Ions are classified by selective ion gating according to their velocity in an electric drift field.

U.S. Pat. No. 3,845,301 issued to Wernlund et al. on Oct. 29, 1974, is directed toward a process wherein plasma chromatograph response time is decreased by improvement of the gas flow. An ion-molecule reaction region is provided in tandem with a larger diameter drift region, and a gas outlet is provided at the junction of the regions. Sample gas flowing through the ion-molecule reaction region into the drift region is re-directed by a counter-flow of drift gas through the drift region, causing both gases to exit through the outlet and reducing intrusion of the sample gas into the drift region. Diffuse gas flow is employed in both regions, special structures being provided to avoid gas jetting.

U.S. Pat. No. 4,855,595 issued to Blanchard on Aug. 8, 1989, discloses an ion mobility spectrometer for detecting ions and for facilitating controlled chemical reactions is described incorporating an inlet for carrier and sample gas, a reaction region having an ionization source and at least two electrodes for generating an electric field and a drift region having at least two electrodes for generating an electric field therein wherein each electrode is coupled to a power supply for placing a predetermined potential on the electrode and wherein each power supply is controlled by an electric field controller for providing a sequence of potentials on each electrode in the reaction region and drift region to control the notion and position of ions in the drift region. The invention claims to overcome the problem of detection sensitivity, detection selectivity and resolution between ions of similar mobility; however enablement of a gridless system is neither taught nor disclosed.

In a later published paper entitled "Ion Injection Mobility Spectrometer Using Field Gradient Barriers, i.e. Ion Wells (Blanchard et al, IJIMS 5 (2002)3, Pp 15-18), a gridless system is disclosed. Blanchard requires the use of a dual zone system for creating a "Trigger well" and a "Storage Well" which must manipulate the voltages at two rings in order to provide an ion reservoir.

These disclosures further illustrate the inability of skilled artisans such as Blanchard and his colleagues to constructively or actually reduce to practice a miniaturized IMS device having highly enhanced sensitivity and performance for the detection of trace chemicals, particularly the relatively high molecular weight, low vapor pressure explosive chemicals.

U.S. Pat. No. 5,162,652 issued to Cohen et al. on Nov. 10, 1992, is directed towards an apparatus and method for the detection and identification of the presence of chosen molecules, typically toxic or contraband located within sealed luggage and the like, comprises subjecting the sealed luggage to a process whereby a portion of the enclosed atmosphere within the luggage is extracted and combined with the surrounding atmosphere in a closed chamber. The extracted, combined sample is passed to a collector, typically a molecule adsorber, which concentrates the chosen molecules by collection on a collecting surface. After the end of a collection period, the adsorbed molecules are released from the surface and passed to an identifier, such as an ion mobility spectrometer. By use of appropriate collection and valving elements, analysis can be accomplished quickly and accurately for a large number of luggage items or the like subject to examination.

U.S. Pat. No. 5,200,614 issued to Jenkins on Apr. 6, 1993, describes an ion mobility spectrometer which employs an electron capture process. A sample gas stream is irradiated to produce positive ions and electrons in an ionization chamber. An open grid electrode is employed in the ionization chamber to maintain a field-free space that claims to allow ion population to build up in the ionization chamber. However, a high electric field is periodically generated across the ionization chamber for periods of less than one millisecond to cause most ions of one polarity in the ionization chamber to be swept out and into a drift chamber. Ions of opposite polarity are discharge on the walls of the ionization chamber. The ions entering the drift chamber travel at drift velocities dependant on their respective charge and mass. A collector electrode is provided for sequentially collecting ions of differing mass, and the collected ion current is transmitted to a signal processing means for measuring intensity and arrival times for the collected ions. A potential can be maintained between the drift chamber and the ionization chamber for preventing ions from traveling down the drift chamber. However, this potential between the drift chamber and the ionization chamber may periodically be switched synchronously with the generation of the field across the ionization chamber to enable ions to pass into the drift chamber during the switching.

U.S. Pat. No. 5,457,316 issued to Cohen et al. on Oct. 10, 1995 relates to an ion mobility spectrometer sensor apparatus which is enclosed in a separate hermetically sealed housing, utilizing a drift gas for the determination of trace contaminants in a carrier gas, including a container for a sample gas containing an analyte the concentration of which is to be determined, means for purifying the sample gas to produce the carrier gas from it, the means for purifying being hermetically connected from the container through a metallic pipe, a source for the purified drift gas which may be the same or different than the carrier gas, an ion mobility spectrometer sensor having a carrier gas entrance and a drift gas entrance and a gas exit, the ion mobility spectrometer sensor being hermetically connected by a metallic pipe from the purifying means and from the source of the drift gas, a back diffusion trap is hermetically connected from the gas exit, and a signal readout is electrically and hermetically connected from the ion mobility spectrometer sensor for electrically sensing and displaying signals obtained in the sensor.

U.S. Pat. No. 6,606,899 issued to Ketkar et al. on Aug. 19, 2003 describes a device for measuring a total concentration of impurities in a sample gas which includes a housing having an inlet to allow the sample gas to enter the housing, an, emitter to generate ions from the sample gas, a field gradient to accelerate the ions toward a collector, the collector adapted to measure total ions, and an outlet to allow the sample gas to exit the housing, whereby a change in total ions received by the collector indicates a change in the total concentration of impurities in the sample gas.

U.S. Pat. No. 6,924,479 issued to Blanchard Aug. 2, 2005 is directed to ion injection in a drift tube apparatus for mobility spectrometry without conventional ion shutters such as the Bradbury-Nielson or similar designs common to such drift tubes. Instead ions were passed between the ion source and drift region by using time-dependent electric field gradients that act as ion barriers between ordinary drift rings. Benefits of this design are simplicity and mechanical robustness. This ion injection technique dynamically accumulates the ions prior to their release into the drift region of the apparatus instead of destroying the ions created between shutter grid pulses, as does the Bradbury-Nielson method. The invention provides not only structural improvements to the well known drift tube apparatus, but also claims to provide inventive methods for operating a drift tube apparatus to achieve maximum analyte injection efficiency and improving ion detection sensitivity. Improving ion detection sensitivity of drift tubes has practical experimental application. Incorporation of the inventive apparatus into a smoke detector is a further practical application of the invention.

U.S. Pat. No. 6,828,795 issued to Krasnobaev et al on Dec. 7, 2004, is directed toward an explosive detection system which detects the presence of trace molecules in air. The sensitivity of such instruments is dependent on the concentration of target gas in the sample. The sampling efficiency can be greatly improved when the target object is warmed, even by only a few degrees. A directed emission of photons, typically infrared or visible light, can be used to significantly enhance vapor emission. The sensitivity of such instruments is also dependent on the method of gas sampling utilized. A cyclone sampling nozzle can greatly improve the sampling efficiency, particularly when the sampling needs to be performed at a distance from the air intake.

What is lacking in the prior art is a teaching of a combination of components which act in concert to provide a miniaturized handheld IMS device having enhanced sensitivity and performance for the detection of trace chemicals. Thus, if a highly sensitive and miniaturized Ion Mobility Spectrometer (IMS) could be produced, with demonstrated performance at elevated temperatures, a long felt need in the art would be met.

SUMMARY OF THE INVENTION

By utilizing the combination of a unique electronic ion injection control circuit in conjunction with a particularly designed drift cell construction, the instantly disclosed ion mobility spectrometer achieves increased levels of sensitivity, while achieving significant reductions in size and weight. The instant IMS is of a much simpler and easy to manufacture design, rugged and hermetically sealed, capable of operation at high temperatures to at least 250° C., and is uniquely sensitive, particularly to explosive chemicals.

A unique ion reservoir is achieved in which ions are temporarily collected prior to injection into the drift region of the IMS. This feature increases the sampled ion population allowing more time for reactions between the reactant ions and sample molecules thus increasing the signal-to-noise parameter as well as over-all sensitivity to a given concentration of sample chemicals. This unique feature allows for better sensitivity while permitting smaller design geometries producing a relatively small device.

In order to achieve an efficient ion reservoir, an innovative electronic ion injection control circuit is provided that is much simpler than current designs for IMS. This circuit operates off of a low voltage trigger timing pulse which trips an opto-isolator. This device is part of an innovative resistive bridge circuit connected to a high voltage transistor. The trigger pulse to the opto-isolator causes the voltage to the base of the high voltage transistor to vary with the pulse. This allows the transistor to provide a sharp square wave voltage pulse to the ion control ring. The resultant large drop in voltage from the pulse causes the ions in the ion reservoir to be injected into the IMS drift region. Between pulses, the ion control ring is in a high voltage condition which stops the ions in the ion reservoir. This circuit, in a very simple and reliable way, enables the high voltage switching (typically between 800 and 1000 volts) to be accomplished, which permits the establishment of the ion reservoir described above.

The above described enhancements produce an added benefit in the form of a gridless IMS design. While the majority of current IMS designs rely on the use of ion control and screen grids to provide a uniform control voltage radially across the ion drift tube; the ion injection circuit as described above operates at sufficiently high voltages such that the use of these grids was found to be unnecessary in the unique IMS drift cell construction subsequently described. Effectuating an embodiment which does not require a complicated grid design greatly simplifies the construction of the IMS and also virtually eliminates microphonic noise pickup. The ion injection circuit above can be thought of as using a "virtual" grid to control the ion movement.

Additionally, a unique IMS drift cell construction is herein provided which employs a hermetic construction using ceramic insulating rings joined to a nickel-cobalt ferrous alloy (such as Kovar®) metal rings by an "active metal" joining process. This ceramic-metal design allows the cell construction itself to be its own enclosure. In prior designs, the IMS drift cell structure was enclosed in an outer housing to isolate it from the operating environment. Since the cell is operated at high voltages, somewhat complicated means had to be provided to electrically insulate the cell from the enclosure. Furthermore, complexities arose in providing high voltage connections to the cell through the enclosure, and to make the signal connections. In the instant design, the metal rings are manufactured with tabs that connect directly to the high voltage control and electrometer board. The hermetic design of the drift tube allows this unique IMS to be used for applications requiring that no outside contaminants be introduced, such as for the analysis of ultra high purity gases. Also, by virtue of the active metal joining process which requires the cell structure to be fired at temperature near 1000° C., all contaminants in the cell structure having any measurable vapor pressures are removed, so that in normal operation the cell does not outgas, and can be stored for lengthy period of time without buildup of contaminants from the slow outgassing of materials as is a problem in many current IMS designs. This novel cell can also be operated at much higher temperatures than current IMSs.

A special cell enclosure which provides for heating the cell, insulating the heated cell from other instrument components, and isolating the cell from spurious electronic signals and interferences is provided to enable the actual mounting and operation of the hermetic drift cell. A thin foil heater was designed to wrap around and heat the cell. The heater is a Kaptan® high temperature plastic sandwich which is electrically insulated when in contact with the cell high voltage rings and does not affect the electrical operation of the cell. This is a novel application of this kind of heater for an IMS cell, and is made possible by the simplified design of the cell itself. Additionally, the heater is controlled using a pulse-width-modulated voltage supply operating at a high frequency so that there are no heater pulses or relay pulses to perturb the IMS signal. Heater pulses are a significant contribution to noise in the spectra of conventional IMS devices. The cell and heater are encased in a special lightweight insulating material which then is contained in a plastic housing. The housing is either coated with a special resistive paint or impregnated with metal so that the housing functions as an electric field shield isolating the cell from outside spurious electrical signal and interferences.

Since the ion reservoir concept allows the concentration of ions and greater ion sampling efficiencies over the standard IMS design, a low level Americium-241 ionization source can be utilized, e.g. as low as 1 microcurie. This has a similar strength as the Am-241 sources employed in commercial smoke detectors, greatly simplifying or eliminating regulatory requirements. However, since the IMS cell requires high temperatures for manufacture, it is not appropriate to do this with the radioactive source installed. Also, the IMS cell may be manufactured at unlicensed facilities, so that the presence of radioactive sources is not permitted at the manufacturing site. For these reasons a unique source design and installation procedure was devised which allows the source to be easily installed at a licensed facility, after the IMS cell body has been made.

A specially coated gas inlet for the IMS was designed which allows for the very efficient inhalation of certain chemicals (specifically explosive molecules and particles). Explosive molecules are by their nature fragile and heat labile. They are also extremely "sticky", so that a delicate compromise has to be determined balancing gas flow rates and the surface temperatures to which the explosive molecules are subjected. The inlet piece is separately heated by the same thin foil heater used to heat the cell. An insulating sleeve made of the same material as used to insulate the cell fits around the heated gas inlet. This inlet configuration is then enclosed in a unique sampling nozzle design, made from a special relatively inert high temperature plastic. Gas ports in the nozzle blow gas at the surface to be sampled at carefully determined angles so that explosives can be efficiently sampled from surfaces. The inhalation inlet allows these trace explosive residues to be effectively introduced into the detector housing of the IMS device for measurement. A unique, single pump gas flow design is employed to both blow air through the nozzle ports, inhale the sampled gas into the IMS inlet, and to provide drift gas flow for the IMS.

Accordingly, it is a primary objective of the instant invention to provide an ion mobility spectrometer which achieves increased levels of sensitivity, while achieving significant reductions in size and weight. The instant IMS is of a much simpler and easy to manufacture design, that is rugged and hermetically sealed, capable of high temperature operation to at least 250° C., and is uniquely sensitive.

It is a further objective of the instant invention to provide an ion mobility spectrometer which incorporates an ion reservoir for providing enhanced sensitivity.

It is yet another objective of the instant invention to teach an electronic ion injection control circuit which enables high voltage switching in a manner which permits establishment of an ion reservoir.

It is a still further objective of the invention to provide an ion mobility spectrometer which is gridless.

It is still an additional objective of the instant invention to provide a drift cell construction for an ion mobility spectrometer which eliminates the introduction of outside contaminants and precludes the formation of outgased contaminants internally.

Yet another objective of the instant invention is the provision of a special cell enclosure for mounting and operation of the hermetic drift cell.

An additional objective of the instant invention is the provision of a low-level ionization source, e.g. AM-241, along with a unique installation procedure.

Yet an additional objective of the instant invention is the provision of a unique sampling nozzle design, which allows for extremely efficient inhalation of contaminants.

Other objects and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

BRIEF DESCRIPTION OF THE FIGURES

FIGS. 14A-E are directed toward the Sample Detector Nozzle, and show details of the nozzle gas port (14A), details of the nozzle design (14B), the nozzle insulator (14C), a perspective exterior view of the nozzle (14D) is shown, as well as a perspective interior view (14E) thereof.

DETAILED DESCRIPTION OF THE INVENTION

Ion Mobility Spectrometry General Description, Operation, and Theory

The IMS, while complex in many of its aspects is conceptually easy to describe. In general terms, it can be thought of as an electronic, gas phase, atmospheric pressure, trace chemical analyzer providing low picogram sensitivity for many chemicals with chemical discrimination based upon ion mobility. Structurally, it is simply an electric field drift tube with an ionizing source, a means for injecting the ions into the drift tube, and an ion collector that electrically measures the ions. In more detail, it is most easy to describe the structure and operation of a standard prior art IMS using a schematic diagram, as set forth in FIG. 1.

In the standard model of the IMS, the drift tube consists of a series of stacked cylindrical rings insulated from each other and ground. The rings are connected to each other in series to a resistive voltage divider, which when a high voltage is supplied, energizes each successive ring in the stack at a uniform progressively lower voltage establishing a uniform linear field gradient along the axis of the drift tube. In some instances, instead of stacked rings, a one piece resistive coated tube has been used, but because of the high resistance required, in practice, these are difficult to manufacture consistently. The high voltage is applied to the source end of the cell; the collector end is near ground potential.

Figure 1:
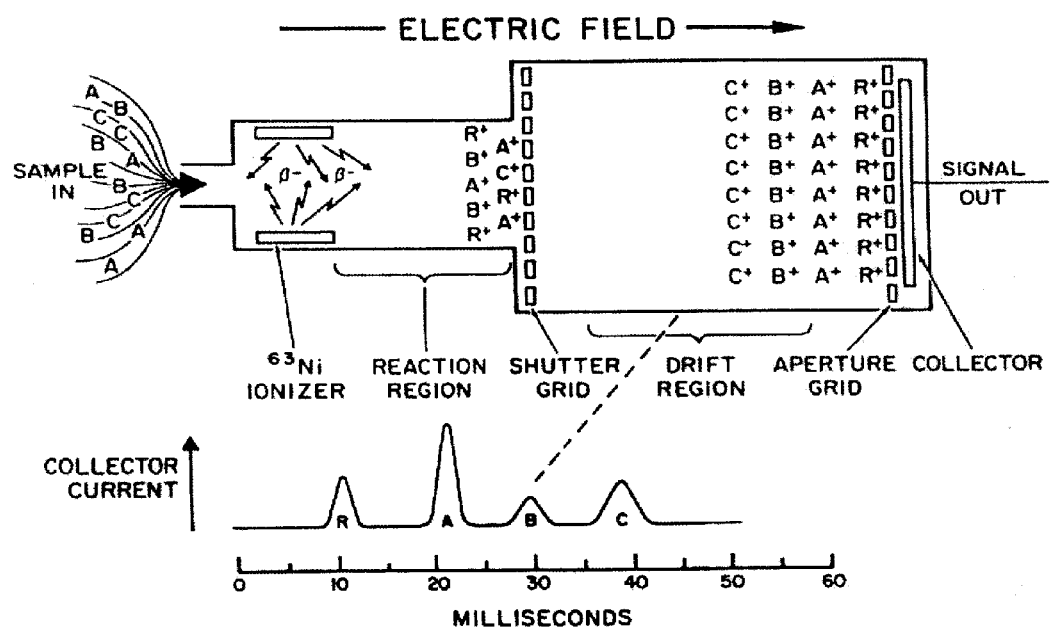
FIG. 1. Schematic Diagram of Standard Prior Art IMS Function.

Normally, the entire cell is at or near atmospheric pressure. Sample vapors enter the ion molecule reaction region as shown in FIG. 1. In almost all configurations of a standard IMS, a radioactive nickel-63 ionization source is used. The typical activity is 15 millicuries. Radioactive sources using tritium or americium-241 have been used, as well as other kinds of ionization mechanisms, such as UV, electrical discharge and coronas, x-rays, and high energy lasers. Ionization of the carrier gas containing the sample vapors results in the formation of certain reactant ions depending upon the nature of the gas. For example, in ambient air the positive ions formed are initially molecular nitrogen and oxygen ions which quickly transfer charge to the water molecules present in ambient air to produce water cluster ions. The negative ions formed are primarily molecular oxygen ions. Ions of both signs are continuously produced in the neutral plasma near the radioactive source, which in the absence of an electric field quickly recombine to their neutral state. Once voltage is applied, the negative and positive ions are separated. If positive voltage is applied, the negative ions are pulled into the source ring at high voltage, while the positive ions are repelled into the drift tube where they follow the electric field gradient toward the collector end of the drift tube. Applying negative voltage reverses the situation, and negative ions move down the drift tube. The positive water cluster ions and negative oxygen ions are called the reactant ions, because they readily and very efficiently react with most trace constituents in the gas to produce the product ions. In the figure, the reactant ions are identified as $R^+$, and the sample molecules as A, B, and C, which become the product ions $A^+$, $B^+$, and $C^+$.

Many ion molecule reactions are very fast and are the reason for the high sensitivity of the IMS technique. Concentrations as low as $10^{-14}$ have been measured using IMS. From a practical standpoint, trace chemical levels in the low picograms ($10^{-12}$ g) or lower can be measured. Another important consideration is that the response is proportional to the reaction time. This has usually been taken to be the drift time of the reactant ion in the reaction region, and is typically just a few milliseconds.

All these ions thus formed move through the reaction region toward the shutter grid. In a standard IMS the shutter grid is of the Bradbury-Nielsen type, which consists of interdigitated wires formed across a ring. Adjacent wires are insulated from each other and normally have small opposite voltage biases applied. If, for example, the shutter grid is at an average potential of 2000V, the two sets of wires may be at 1985V and 2015V, having a bias voltage of ±15V applied relative to the shutter grid average voltage. Since the wires are closely spaced, relatively high electric fields are established near the wires radially to the main drift tube field gradient. Ions moving to this grid are rapidly attracted to one set of wires and discharged. Thus the grid in its "closed" condition stops all ions from moving farther into the drift tube. To "open" the grid, the voltage biases to the wires are removed, and the ions follow the drift tube field gradient into the drift region. There is some ion loss due to ions hitting the wires, but very fine wires are used, typically providing an optical transparency of 80% or more to the grid. The grid is then repetitively opened for short intervals admitting pulses of the mixed ions into the drift region. The functioning of the shutter grid operates on millisecond time frames. Typically, the shutter grid is opened every 20 to 50 msec for about 0.2 to 0.5 msec. Needless to say, the construction of the shutter grid and the required control circuitry is very complex, and has been historically the most difficult to manufacture and costly component in ion mobility spectrometers. Additionally the fine, taught wires used are microphonically sensitive, so that the shutter grid operates as an acoustic microphone, contributing noise to the ion mobility spectra from any outside vibrations.

Returning to the figure, as the mixed pulse of ions move down the drift tube they separate into their different chemical ion species base: upon their differing mobilities in the drift medium, typically air. Usually the air in the drift region is moving in a counter-current direction to the ion flow. The drift gas generally does not contain the sample molecules, which effectively quenches the ion-molecule reactions that occur in the reaction region. This allows for the clean separation of peaks in the drift region. The individual ion species can be thought to chromatographically separate in the "stationary phase" of the drift medium. Thus the early name for IMS, plasma chromatography, was used because a plasma was formed which was then separated chromatographically. Whereas a gas or liquid chromatograph typically produces chromatograms in minutes, the "plasma chromatography" produced "chromatograms in milliseconds. The name ion mobility spectrometry was taken up early on to indicate many of the similarities between IMS and mass spectrometry. The IMS can be thought of as being a time-of-flight mass spectrometer operated at atmospheric pressure. The IMS does not have the resolution of a mass spectrometer, but it is much less complex and in many applications actually has greater sensitivity.

Molecular weight and ionic cross section (shape) both affect mobility. Under the applied field the ions undergo thousands of collisions with the air molecules they encounter, which causes the ions to move at an average terminal velocity as opposed to continuously accelerating in the electric field. Within each pulse of ions, diffusion processes cause the ion pulse to acquire a bell curve or semi-gaussian shape. The arrival of the individual pulses at the collector electrode produces a characteristic ion arrival time spectrum as shown in the figure. The collector is almost always of the Faraday type, and is connected to a fast electrometer which converts the very small ion currents to sensible voltages which can then be read out on an oscilloscope to view the spectra. Modern data processing techniques allow the rapid recording and viewing of the spectra. Since the spectra are generated so quickly, typically a number of spectra are accumulated and signal-averaged to improve signal-to-noise. Fifty 20 msec spectra, for example produce an averaged spectrum every one second or so, which is usually more than sufficient for most applications.

Operation and Advantage of Ion Reservoir Design:

In the instantly disclosed miniaturized IMS, a different approach has been taken to produce and inject the ions into the drift region. The shutter grid has been eliminated, but the equivalent ring does the same function by having a relatively high voltage applied to it, thus reversing the field at this point to stop the ions. The level of field reversal has to be quite high to accomplish this. The effect of doing this is to create an ion reservoir in the space above the high potential ring. To take an example; if 1000V is applied to a drift tube 10 cm long with rings spaced at 1 cm intervals, then the voltage difference between each ring would be 100V. The source ring would be at 1000V, the next ring down would be at 900V, the next at 800V, and so on to produce a uniform field gradient down the tube. If then, say the $5^{th}$ ring down instead of being at 600V were set to 800V, then the sequence of ring voltages down the cell would be: 1000V, 900V, 800V, 700V, 800V, 500V, 400V, etc. The $4^{th}$ ring at 700V now is at low potential relative to the rings above and below it at 800V. The ions moving down the tube from the source would stop at this low potential area. However, the source is continuously producing ions which march down the drift tube until the low potential area is encountered, where they "pile up" on top of the ions already there. Thus, the ions accumulate in this low potential reservoir. The population of ions in the reservoir is dynamic in that the flow of incoming ions is eventually balanced by the loss of ions to the walls of the drift tube primarily through diffusion. If the ion concentration becomes high enough, space charge and mutual repulsion effects can also limit the ion concentration. Diffusion can be shown to operate on time frames multiple 10s of milliseconds, so that if the ion population is sampled every 20 msec or so, most of the accumulated ions are still present in the reservoir. The reservoir is sampled and injected into the drift region by reverting the higher potential $5^{th}$ ring from 800V to 600V which then reestablishes the uniform field gradient down the drift tube. The mixed ions in the reservoir then move into the drift region and separate into individual ion peaks as previously described for the standard IMS. The cell voltage remains uniform for a sufficient time to allow the all the ions in the reservoir to move past the $5^{th}$ ring into the drift region of the cell. In practice this time is 1 to 5 msec. Then the higher potential is reapplied to the $5^{th}$ ring and the process repeats. Typically, the reservoir is sampled every 20 msec, which gives enough time for all the ion peaks to be measured.

The ion reservoir technique has a number of important consequences apart from providing an alternative to the standard shutter grid technique. In the standard IMS the shutter grid is only opened for typically 1% of the time. This means that only 1% of the ions being generated at the source are actually sampled. 99% are lost. Also, the reaction time for the production of sample ions is only the relatively short time it takes a reactant ion to traverse the length of the reaction region. With the ion reservoir, proportionally a much greater number of ions are available to be measured. Theoretically, this could be 100%, but in actuality losses in the reservoir reduce this number. Additionally, as the ions reside in the reservoir between sampling intervals, the reactant ion has more time to react with the sample molecules. Both of these effects increase the inherent sensitivity of this technique to any given level of sample chemicals over the standard model.

The increase in the number of ions sampled usually does not lead to a great increase in the sensitivity of IMS due to two factors: the signal-to-noise improvement is not usually proportional to the increased number of ions sampled, and for the relatively energetic nickel-63 sources used, the space charge repulsive effects can limit the ability to appreciably concentrate ions in the reservoir. However, the capability of utilizing the ion reservoir does allow the use of a less energetic source. In prototype work a 0.9 microcurie americium-241 source was used with excellent results. In the instantly disclosed miniaturized IMS, for mechanical reasons, a 20 microcurie americium-241 source is used. The peak intensities observed using this source with the ion reservoir are equivalent or better than observed in a standard IMS using 15 millicuries of nickel-63 having almost 1000 times the activity.

Also, because of the longer reaction times available, the length of the reaction region can be greatly reduced, and the entire drift tube miniaturized. The volume of the instant IMS is about 5% that of a standard IMS, with a concomitant reduction in weight, as well. Smaller volumes have practical measurement advantages, because less gas is used to operate and clear the drift tube. The use of the ion reservoir also greatly simplifies the control electronics.

Figure 2:
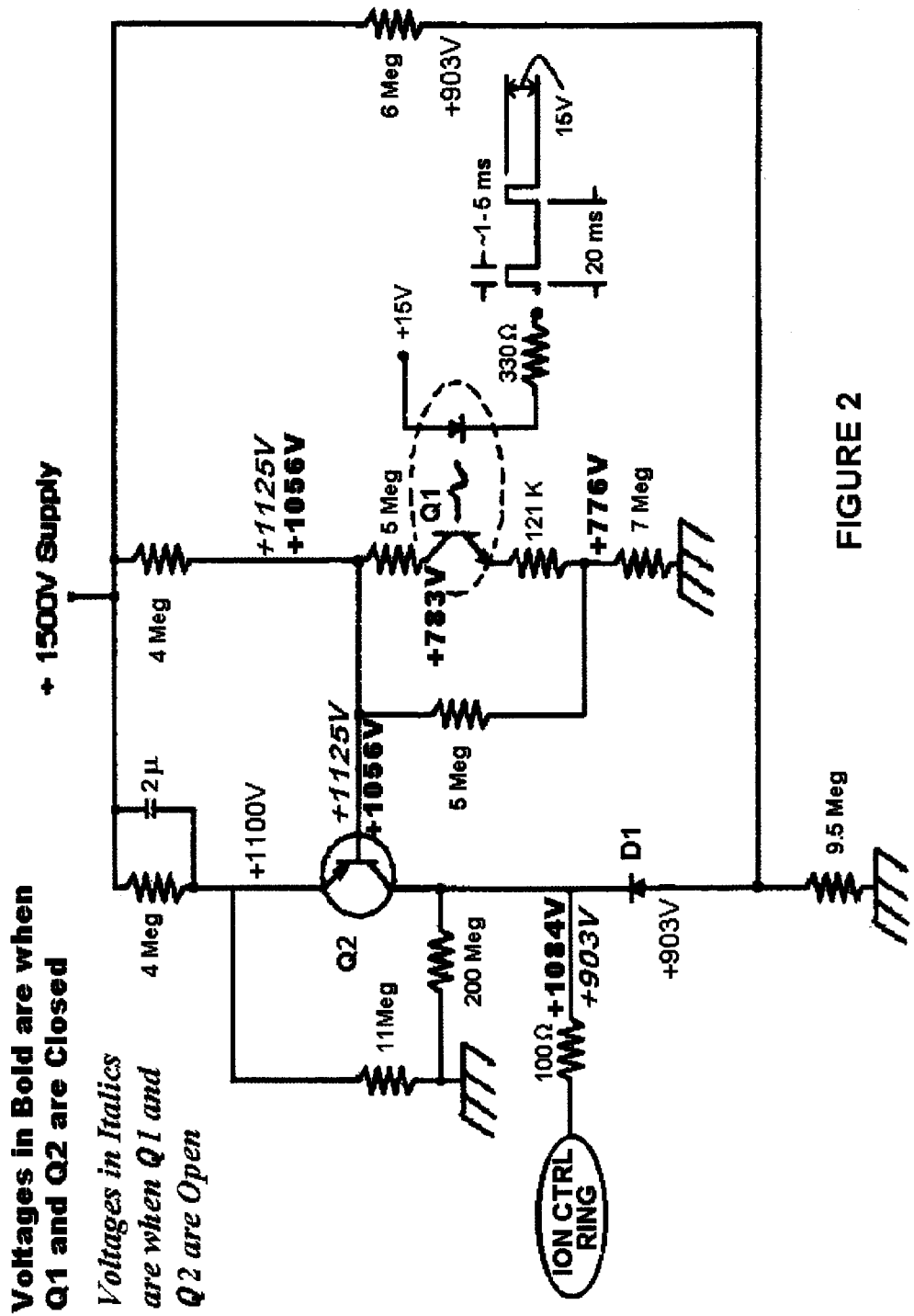
FIG. 2. Typical Ion Control Circuit Design.

Description of Electronic Ion Injection Control Circuit:

The electronic ion injection control circuit useful in the instantly disclosed IMS is illustrated in FIG. 2. The functioning of this circuit is controlled by a low voltage trigger timing pulse as shown in the figure. This trigger pulse can be generated externally in a variety of ways, such as from a trigger circuit or from a computer generated pulse. The trigger pulse should have the form of a square wave with an amplitude of +5V to +15V, a repetition period of typically 10-50 msec, and a pulse width of 1-20 msec. Although, in order to generate proper peaks in the IMS from the ion reservoir, the pulse width required has been experimentally shown to be from 1 to 5 msec in duration.

The organization of a generic ion control circuit of our design can be seen in FIG. 2. In this particular circuit, high voltage is supplied from a +1500V power supply. There are three legs coming from the +1500V power supply. Each leg has its own path to the three grounds shown. The legs marked with +903 volts and +1100 volts voltage labels are separate due to the action of Q2, a high voltage PNP transistor, and the diode, D1. Because the leg with the italicized voltage values only contacts the +1100 volt leg at the base of Q2, this also has an independent ground. Considering first the situation when Q1 and Q2 are both open, then the +1100 V, italicized and +903 voltage labels apply. In this condition, the voltage paths are relatively simple. The left hand +100V leg has a total resistance value of 15 Megohms. The center italicized leg has a resistance value of 16 Megohms. The right hand +903V leg has a total resistance of 15.07 Megohms, due to the effect of the 200 Megohm resistor and the 9.5 Megohm resistor being in parallel when Q2 is open. The calculated voltages at various points in the circuit are shown on the figure. For instance, the 4 Megohm resistor at the top of the left hand leg coming down from the +1500V power supply then provides a 400V (4÷15=0.26667, ×1500V=400V) voltage drop, setting the voltage below this resistor at +1100 V, as shown. This is the voltage supplied to the emitter of the transistor Q2. Since, in this condition, the base of Q2 is at +1125, and is greater than the emitter voltage of +1100 V, Q2 is in an open condition (base more positive). With Q2 open, the voltage to the control grid through the diode D1 is calculated to be +903V. This is the open position for the ion control ring, allowing ions to pass into the drift region of the cell, This condition holds during the 1 to 5 msec trigger pulse to Q1.

Q1 is a high voltage opto-isolator. The action of the low voltage trigger pulse opens or closes Q1 to the passage of current. When Q1 is closed, then there is a parallel resistance path formed on the italicized leg. There are now 5 Megohms in parallel with 5.121 Megohms (neglecting the resistance of Q1). This yields an equivalent resistance for the two branches together of 2.53 Megohms. Thus, the total resistance of the italicized leg drops from 16 Megohms to: 4 Megs+2.53 Megs+7 Megs=13.53 Megohms. Now, the 4 Megohm resistor at the top of this leg provides a greater percentage voltage drop from the +1500V supply with the total resistance reduced to 13.53 Megohms. This voltage drop is 444V which sets the voltage below this 4 Megohm resistor at +1056V as indicated by the bold voltage values. Since the voltage supplied to the base of Q2 in this condition of +1056V is now less than the emitter voltage of +1100 V, Q2 closes, which provides an alternate voltage path to the ion control ring. The 200 Megohm resistor is now in parallel with the 11 Megohm resistor on the left hand leg, which sets the voltage to the ion control grid at +1084V, as shown. The diode D1 prevents communication to the +903V of this leg isolating this voltage from the ion control ring and permitting proper functioning of the circuit. The control grid voltage varies between 903V (open to ions) and 1084V (closed to ions) with the operation of the trigger pulse.

Thus, as described before, this circuit, by means of the actions of the low voltage trigger timing pulse, the high voltage opto-isolator, and the resistive bridge circuit connected to a high voltage transistor, allows this transistor to provide a sharp square wave voltage pulse to the ion control ring. The large drop in voltage from the pulse causes the ions in the ion reservoir to be injected into the IMS drift region. Between pulses, the ion control ring is in a high voltage condition which stops the ions in the ion reservoir. This circuit, in a very simple and reliable way, enables the high voltage switching (in this example between +903V and 1084V) to be accomplished, which effectively permits the establishment of an ion reservoir; which heretofore was not possible following the teachings of the prior art, e.g. Blanchard's U.S. Pat. No. 4,855,595.

The 121 K ohm resistor in series with Q1 is used to protect it from high currents, allowing a voltage drop of only 7V. The current through Q1 calculates as 1500V÷13.53 Megohms=110 microamps. The current through the closed Q2 and down the 200 Megs to ground is only 5.7 microamps. These low currents also enable miniaturized surface-mount-technology, SMT, components to be used greatly lowering the cost of producing this circuit. Q1 cannot be used by itself to set the voltages to the ion control ring, because this component alone cannot provide the proper high voltage pulse peak shape. It also may be that because of the relatively large voltage differences required, the voltage and current limits the miniature opto-isolators are close to being exceeded. The opto-isolator provides the few microseconds of quiescent state that the base of the transistors need for settling time. It also aids in extending the life of the switching transistors, as well as providing isolation between the high voltage and low voltage trigger pulse. The circuit as described here permits only a small voltage change of 69V to the base of the transistor to accomplish a 181 V voltage change to ion control ring. The circuit described can be easily switched to a negative voltage circuit by changing the transistor from PNP to NPN, and reversing the direction of the diode D1.

All of the resistor values and voltages used can be changed somewhat to vary the voltages supplied to the ion control grid to optimize performance in any given analysis application, but the essentials of this circuit remain unchanged. In addition, a 1 Megohm resistor can be added in series with the 200 Megohm resistor shown in FIG. 2 to provide a low voltage test point to monitor the actual voltage characteristics of the ion control ring.

Various voltages have been used for the positive ion circuits depending upon the application. For instance, for the NASA project operating in helium, the ion control and voltage divider circuits were run at +345 V and +280 V respectively. Due to the low breakdown potential of helium, lower voltages are required in order to eliminate possible arcing. The circuits performed fine over these ranges of voltages.

Figure 3:
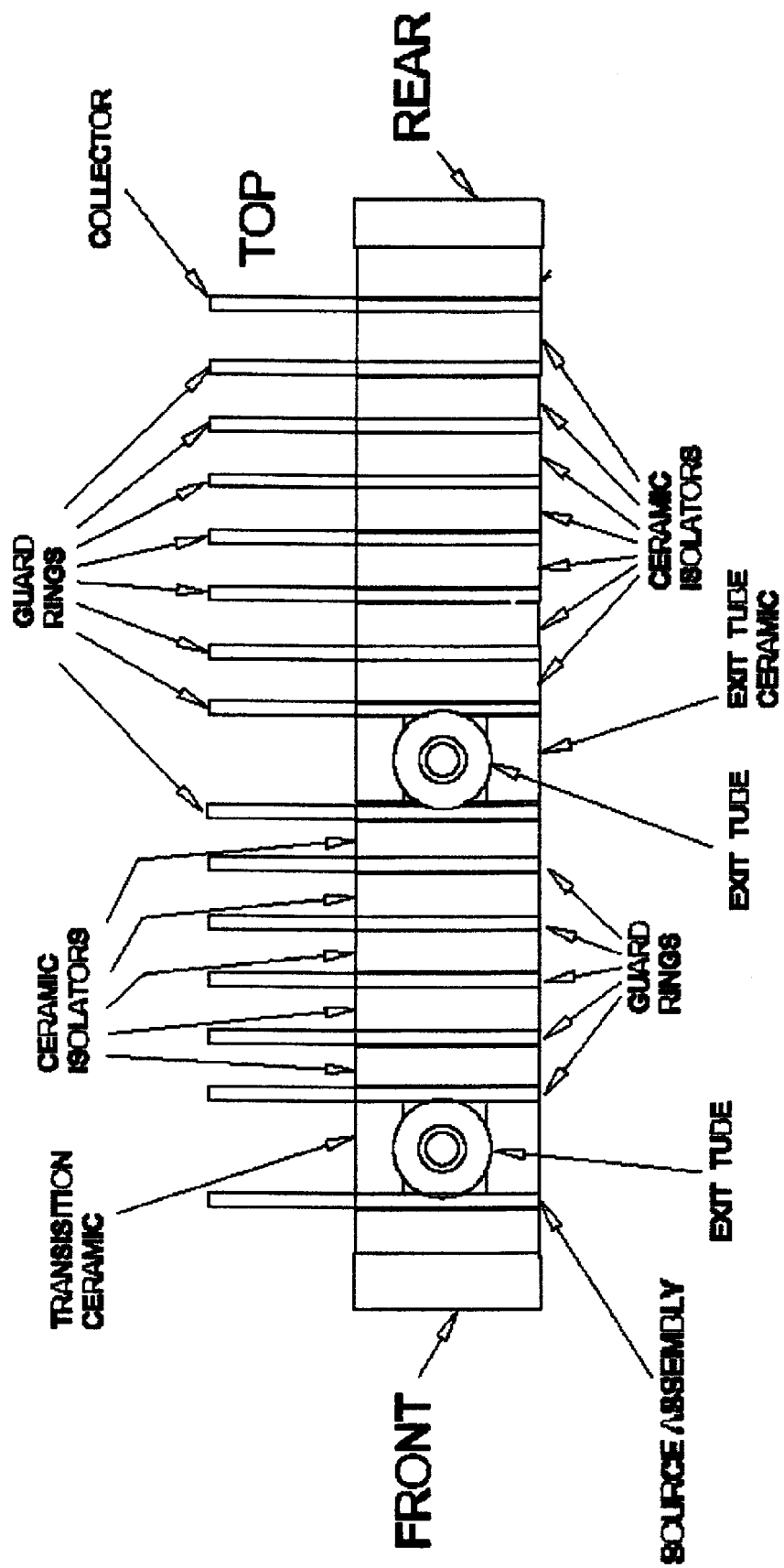
FIG. 3. Design Schematic of Explosives Detection Drift Cell.
Figure 4:
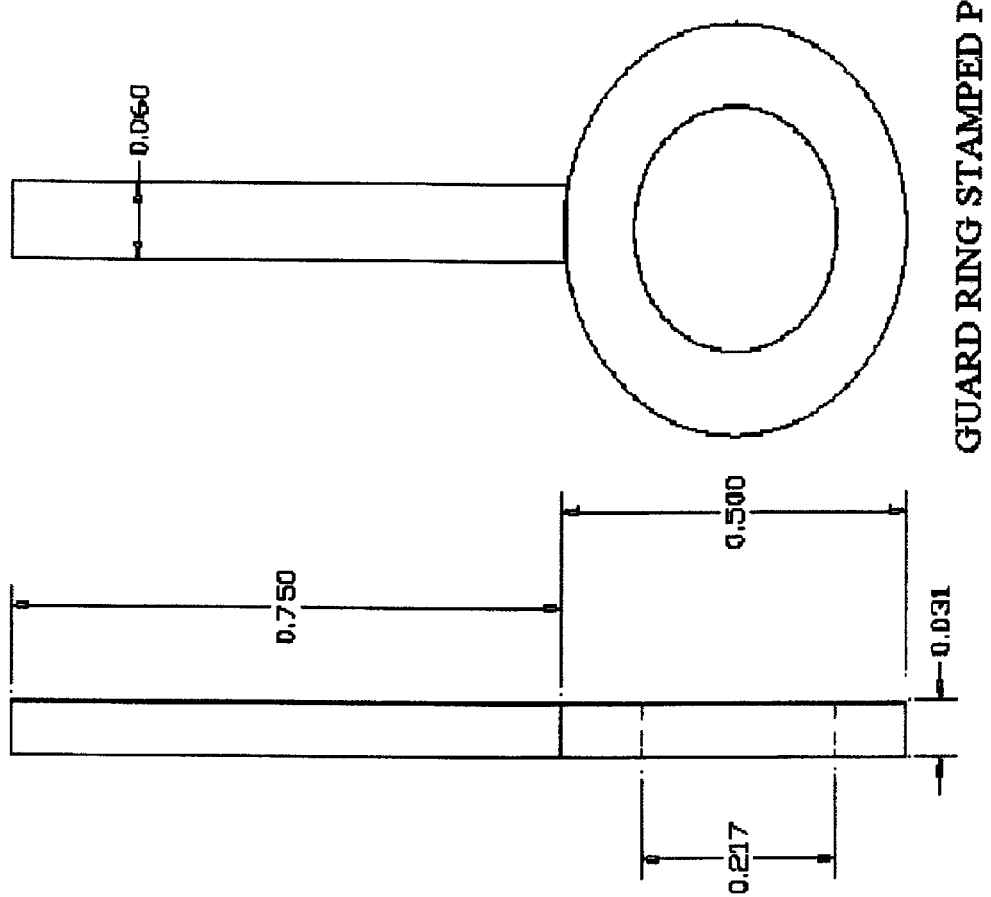
FIG. 4. Guard Ring.

IMS Drift Cell Construction:

The ion detection assembly includes a unique IMS drift cell construction which employs a hermetic construction using ceramic insulating rings joined to Kovar® metal rings by an "active metal" joining process. This process is commercially available from various companies, and the particular process used for the fabrication of prototypes was proprietary to the fabricator. This ceramic-metal design allows the cell construction itself to be its own enclosure. FIG. 3 shows the a prototype design structure or the explosives detection drift cell. The active metal brazing process achieves a permanent bond between a proper metal such as Kovar® and a high grade alumina based ceramic, using a firing fixture. The process is relatively quick and simple. A number of design innovations were incorporated into the drift cell construction for both performance improvements and to simplify fabrication. It was learned that the Kovar® rings could be stamped to include a tab for making the electrical connection. The design of this is shown in FIG. 4. This piece was quite thin with a thickness of only 0.031". This had three advantages. The thin Kovar® pieces are less costly to produce, put less strain on the ceramic during the joining process, and should provide a more uniform field in the IMS cell. Thicker metal guard rings produce larger "steps" in the field gradient. Thin guard rings produce a more uniform field. Having the tab stamped as part of the ring greatly simplified assembly of the cell since it was no longer required to either weld the tabs onto the rings or to spot weld the connecting wires. The tabs are designed to be plugged directly into a circuit board containing the resistive bleeder string.

It was determined that the preferred procedure is to use Kovar® rings and ceramic spacers with the same outer dimensions. This allows a simple fixture to be used to build the cell. The diameters of the rings and spacers could now be the same because the tabs on the rings allow the electrical connections to be easily made. This also makes engineering the heater design very easy because the cell can be easily placed in an insulated heater block which contacts all the surfaces of the cell for proper heating. The ceramic inner wall is at a distance from the inner edge of the metal guard ring which should also reduce any static effects on the voltage gradient field.

Figure 5:
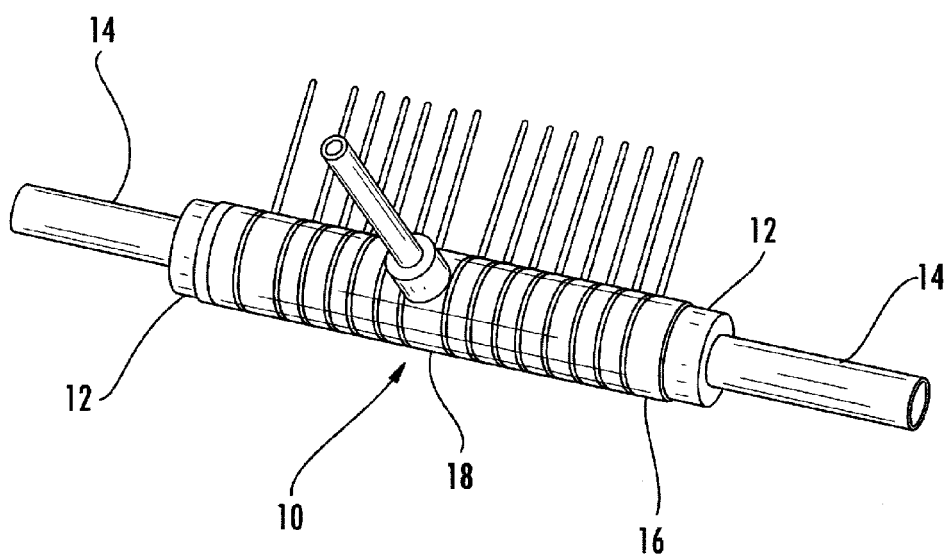
FIG. 5. Pure Gas Analysis Prototype Drift Tube.

The ceramic and Kovar® parts are assembled vertically, piece by piece, in a firing fixture. The fixture containing the yet unbrazed assembly is then placed in a furnace at approximately 1000° C. to complete the active metal brazing process. FIG. 5 shows a version of the drift cell which can be used for pure gas analysis. The end caps and side tubes required careful considerations in their design to prevent fractures and contamination during the firing process. The end tube pieces were designed so that they had a shallow cap which then could fit over a step machined on the end of the mating ceramic end piece. In this way the brazing was done on the diameter rather then the flat. This produces compressive stresses during firing or cooling, which the ceramic easily tolerates.

As can be seen in the explosives detection drift cell drawing shown in FIG. 3, the side tube was designed to fit over a boss formed on the appropriate ceramic spacer. This was either the center spacer as shown in FIG. 5, or also included the spacer near the inlet as shown in the FIG. 3 drawing. This boss had a step at the end so that a Kovar® stub could fit over it, similarly as the end tubes. As shown in FIG. 5, a ⅛ inch stainless steel tube was then welded to the Kovar® stub. This design provides a rugged construction with the brazing done on the relatively large outside diameter of the ceramic boss.

The end caps were of two designs. One type is shown in FIG. 5. The end caps have ¼ inch stainless steel tubes welded on to them, to which gas tight (typically VCR) fittings can be welded in order to make a completely gas tight cell for analysis of high purity gases. The other type of end caps are shown in the explosives detection drift cell drawing (FIG. 3). These caps are tapped for ⅛ inch Swagelok® fitting threads. A ⅛ inch Swagelok® union elbow could then be threaded into the rear end cap, and the inlet fitting threaded into the inlet cap.

Another very important feature of the ceramic-metal design is the use of very high resistance ceramic components. The electrometer and ion detection circuit of this IMS is exceedingly sensitive, being capable of measuring femtoamps. The cell is operated at high voltages, so that very small leakage currents through the cell insulators can be a great problem. It has been calculated that the ceramic insulators need to provide 10,000 megohms of resistance for best performance.

In prior designs of the ion detection assembly, the IMS drift cell structure was enclosed in an outer housing to isolate it from the operating environment. Since the cell is operated at high voltages, somewhat complicated means had to be provided to electrically insulate the cell from the enclosure. Also further complexities arose in providing high voltage connections to the cell through the enclosure, and to make the signal connections. IMS cells are normally difficult to manufacture due to their complexity and the stringent electrical and cleanliness requirements of the technique. The prior art fails to teach a design that is as inherently simple, rugged, and clean as the herein disclosed design. This ceramic-metal design allows the cell construction itself to be its own enclosure. The hermetic design of the drift tube allows this unique IMS to be used for applications requiring that no outside contaminants be introduced, such as for the analysis of ultra high purity gases. Also, by virtue of the active metal joining process which requires the cell structure to be fired at temperature near 1000° C., all contaminants in the cell structure having any measurable vapor pressures are removed, so that in normal operation the cell does not outgas, and can be stored for lengthy period of time without buildup of contaminants from the slow outgassing of materials as is a problem in many current IMS designs. This novel cell can also be operated at much higher temperatures than current IMSs.

Mounting and Operation of the Hermetic Drift Cell:

The actual mounting and operation of the hermetic drift cell makes use of a special cell enclosure which provides for heating the cell, insulating the heated cell from other instrument components, and isolating the cell from spurious electronic signals and interferences. Again, the enclosure provides superior performance at a very low weight, just a few grams.

Figure 6:
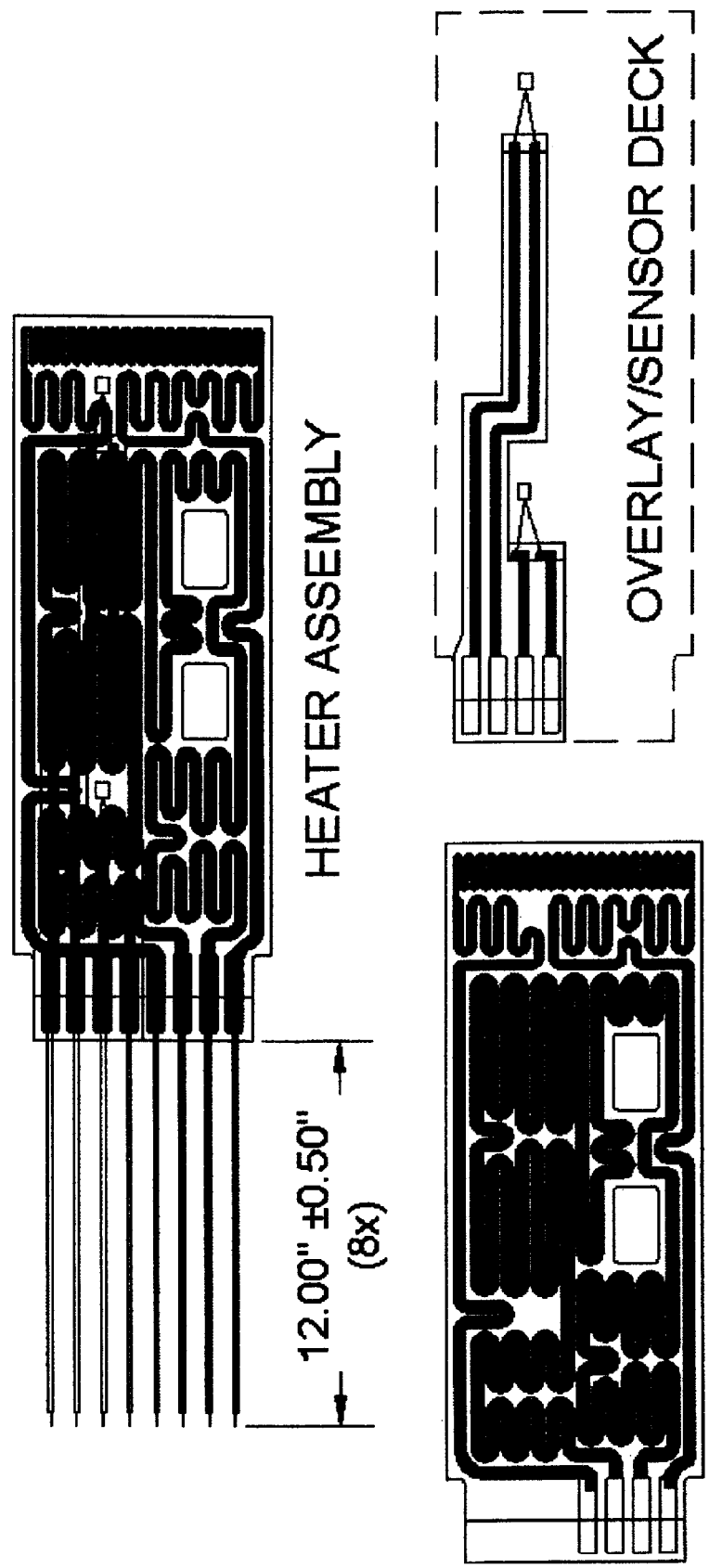
FIG. 6. Heater Schematic.

A thin foil heater was designed to wrap around and heat the cell. The heater is a Kaptan® high temperature polyimide plastic sandwich which is insulated itself electrically from the cell high voltage rings and does not affect the electrical operation of the cell. The particular heater used in the prototype development work was made by Thermal Circuits Inc. of Salem, Mass. A schematic of this heater is shown in FIG. 6. The heater elements cover virtually the entire surface of the heater. This thin foil heater has two separate heater zones which allow the drift cell body and inlet to be independently heated. The heater zones are designed so that more power is supplied to the inlet, where heat losses are higher. As can be seen in the drawing, this heater was composed of two decks, one for the heater elements, and one for the RTD temperature sensors. The temperature sensors consist of 100 ohm platinum RTDs. This is a novel application of this kind of heater for an IMS cell, and is made possible by the simplified design of the cell itself. Additionally, the heater is controlled using a pulse-width-modulated (PWM) voltage supply operating at a high frequency so that there are no heater pulses or relay pulses to perturb the IMS signal. Heater pulses are a significant contribution to noise in the spectra of conventional IMS devices. The heater control is handled by a microprocessor which reads the RTDs and sets the PWM frequencies to provide the correct temperatures. The thin foil heaters are flexible and light weight, and easily wrap around the cell and install into the insulator block.

The cell and heater are encased in a special lightweight insulating material which then is contained in a plastic housing. The housing is either coated with a special resistive paint or impregnated with metal so that the housing functions as an electric-field shield, isolating the cell from outside spurious electrical signals and interferences. The insulating material is ZIRCAL-18 Refractory Board, manufactured by Zircar Refractory Composites, Inc. of Florida, N.Y. This is a high temperature calcium silicate block insulation with excellent mechanical properties that combines relatively high strength and excellent thermal insulating characteristics. At 200° C. the ZIRCAL-18 has about twice the thermal conductivity of still air. When used with the heated Mini-Cell, very satisfactory results were obtained. The outside of the insulator block approaches 45° C., when the cell was operated at 200° C., but this is still very acceptable. One further advantage of the ZIRCAL-18 is that it is a relatively strong material that is easily machined.

Figure 7:
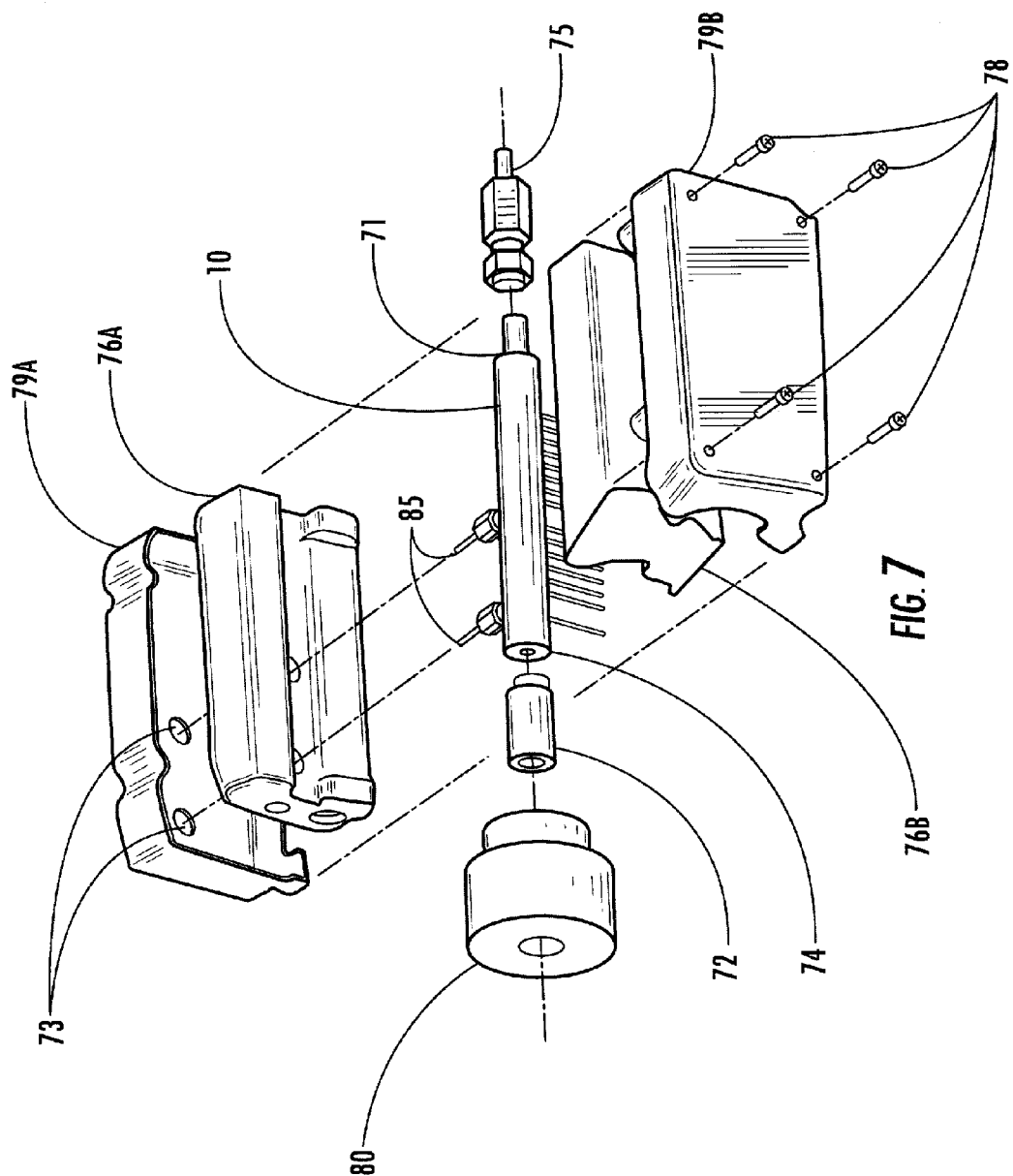
FIG. 7. Cell Enclosure Assembly Exploded View.

FIG. 7 shows the assembly of the cell enclosure inclusive of the drift cell 10, insulator housing 79A having exit port holes 73, and insulator housing 79B for receipt of fastening screws 78 therethrough. To the drift cell 10 are mounted threaded receiver gas connector 71, to which swagelok fiting 75 is coupled. On its opposite end drift cell 10 is in fluid engagement with stainless steel sample inlet 72, which is threadably connected to receiver 74. Sample nozzle 80 is in turn fluidly coupled to sample inlet screw 72. Detector insulators 76A and 76B are sandwiched about drift cell 10 and encased by housings 79A and 79B upon assembly.

Ionization Source Design and Installation:

Since the ion reservoir concept allows the concentration of ions and greater ion sampling efficiencies over the standard IMS design, a low level Americium-241 ionization source 83 (see FIG. 8A) could be used. This has a similar strength as the Am-241 sources employed in commercial smoke detectors, which greatly simplifies or eliminates regulatory requirements for the instant IMS. However, since the IMS cell requires high temperatures for manufacture, it is not appropriate to do this with the radioactive source installed. Also, the IMS cell may be manufactured at unlicensed facilities, so that the presence of radioactive sources are not permitted at the manufacturing site. For these reasons a unique source design and installation procedure was devised which allows the source to be easily installed at a licensed facility, after the IMS cell body has been made.

Figure 9:
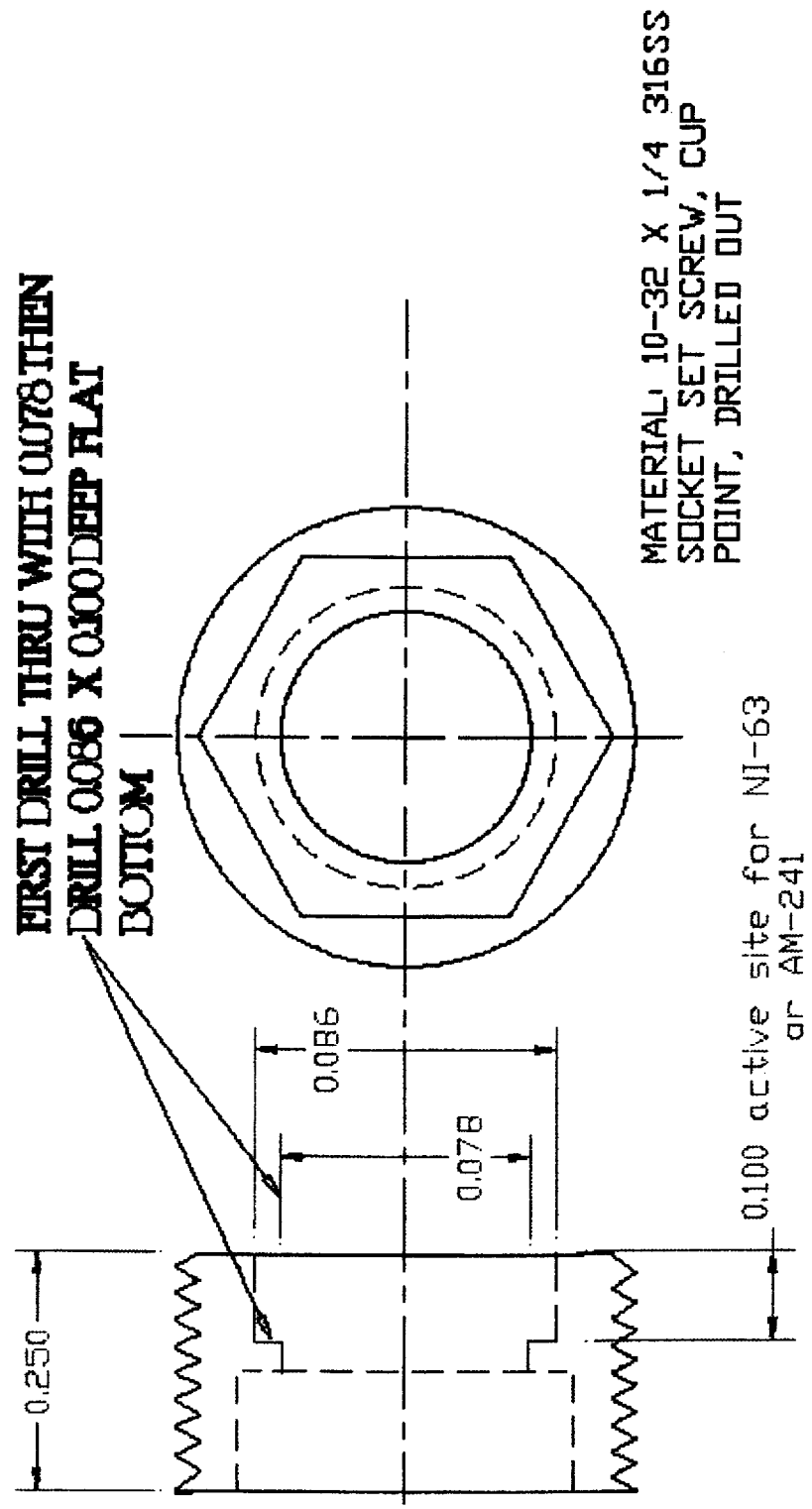
FIG. 9. Source Holder.
Figure 10:
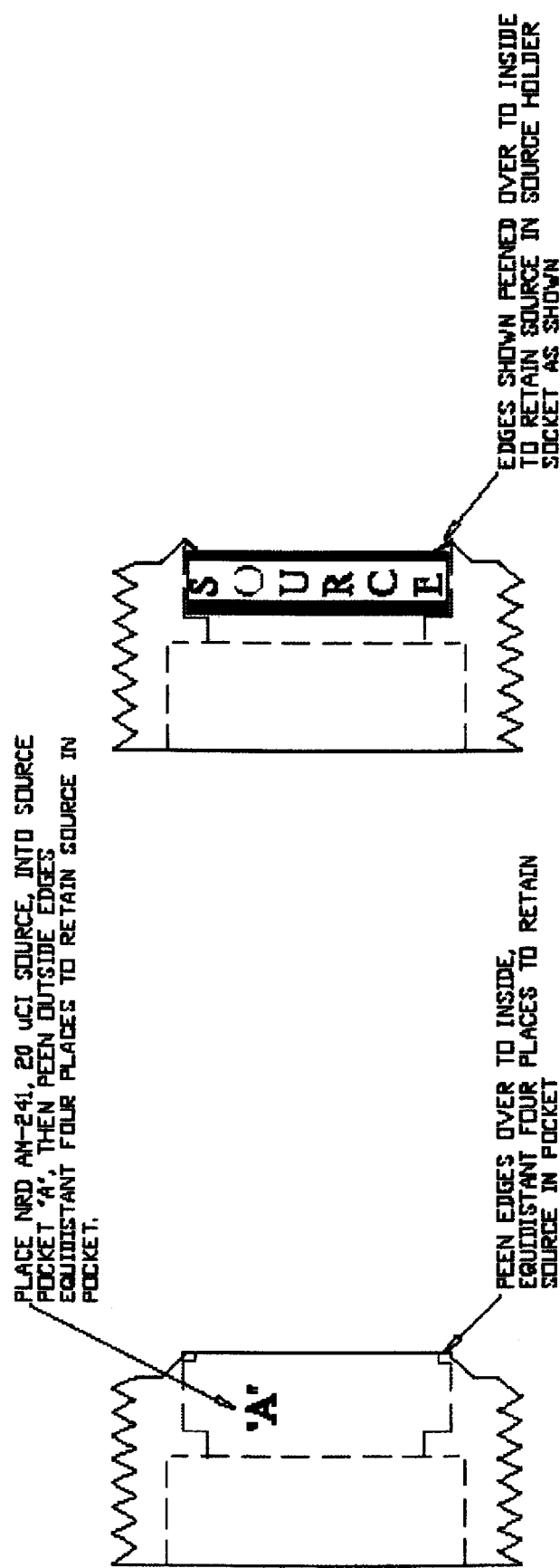
FIG. 10. Source Assembly.

FIG. 8A relates to a drift cell assembly, and includes an expanded view inlet assembly 81, and source holder 82, as it communicates with the drift cell 10, the drift cell having exit ports 85, as well as the collector assembly 88. The expanded view of inlet assembly 81 illustrates the radioactive source 83, positioned within source holder 82, in the explosive detection drift cell 10. FIG. 8B shows an assembled view of inlet assembly 81. FIG. 8C is a sideview of drift cell collector assembly 88, and FIG. 8D further shows the detail of the hole configuration 87 of the collector assembly, which prevents direct access to the source from the rear end of the drift cell assembly 86. There are a number of components relative to the installation of the source as shown by the subsequent drawings. FIG. 9 shows the source holder, which is a standard 10-32 stainless steel socket head screw with a cup point that has been drilled out as shown in the drawing. These are sent to a purveyor of radiation materials and ionization sources, e.g. NRD LLC, which installs a 20 microcurie americium-241 foil into the source holder as shown in FIG. 10.

Figure 8:
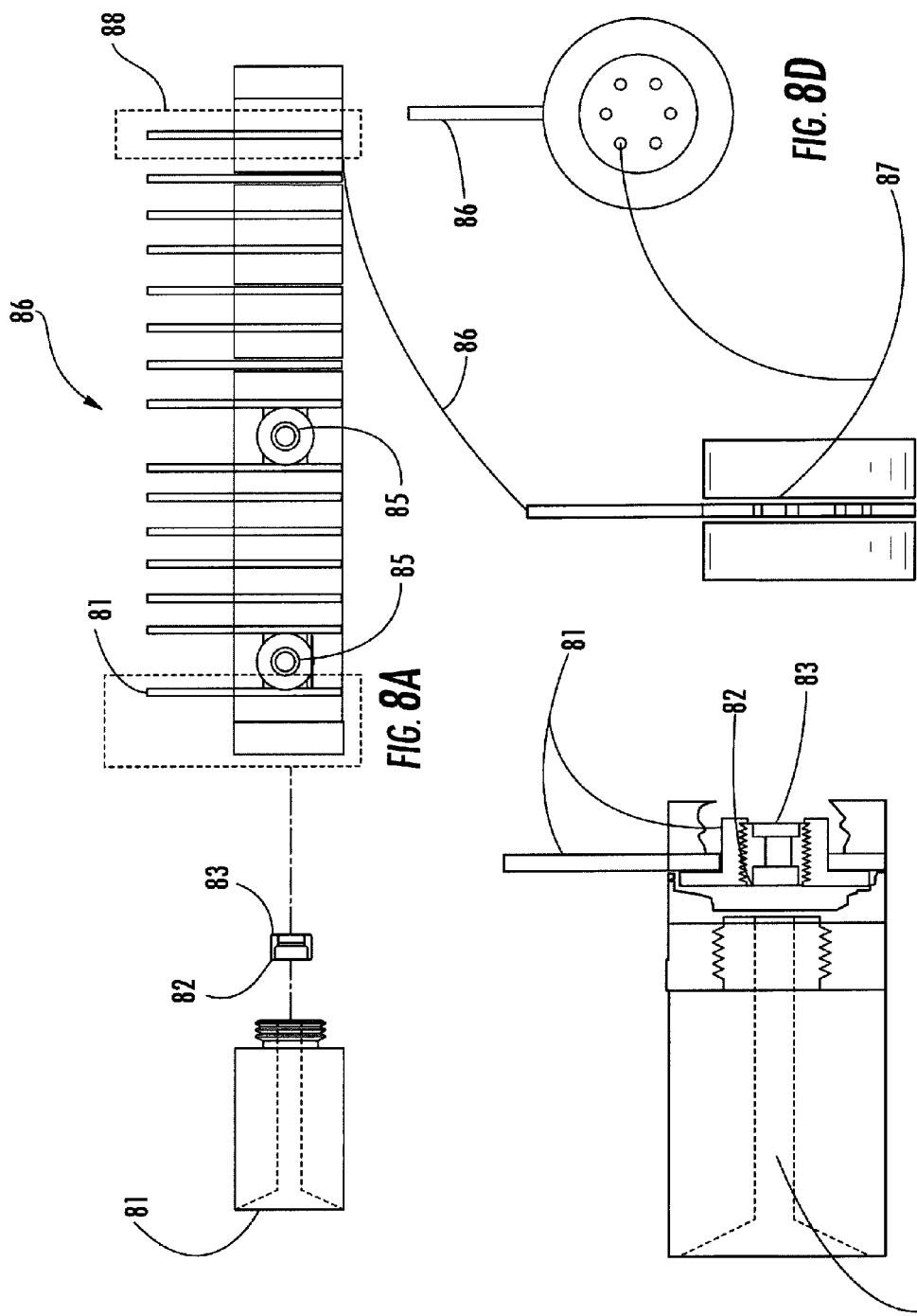
FIG. 8A relates to a drift cell assembly, and includes an expanded view of the source holder, as it communicates with the drift cell, as well as the collector assembly.
FIG. 8B is an assembled view of the source holder.
FIG. 8C is a side view of the drift cell collector assembly.
FIG. 8D is a detailed view of the collector assembly hole configuration.
Figure 11:
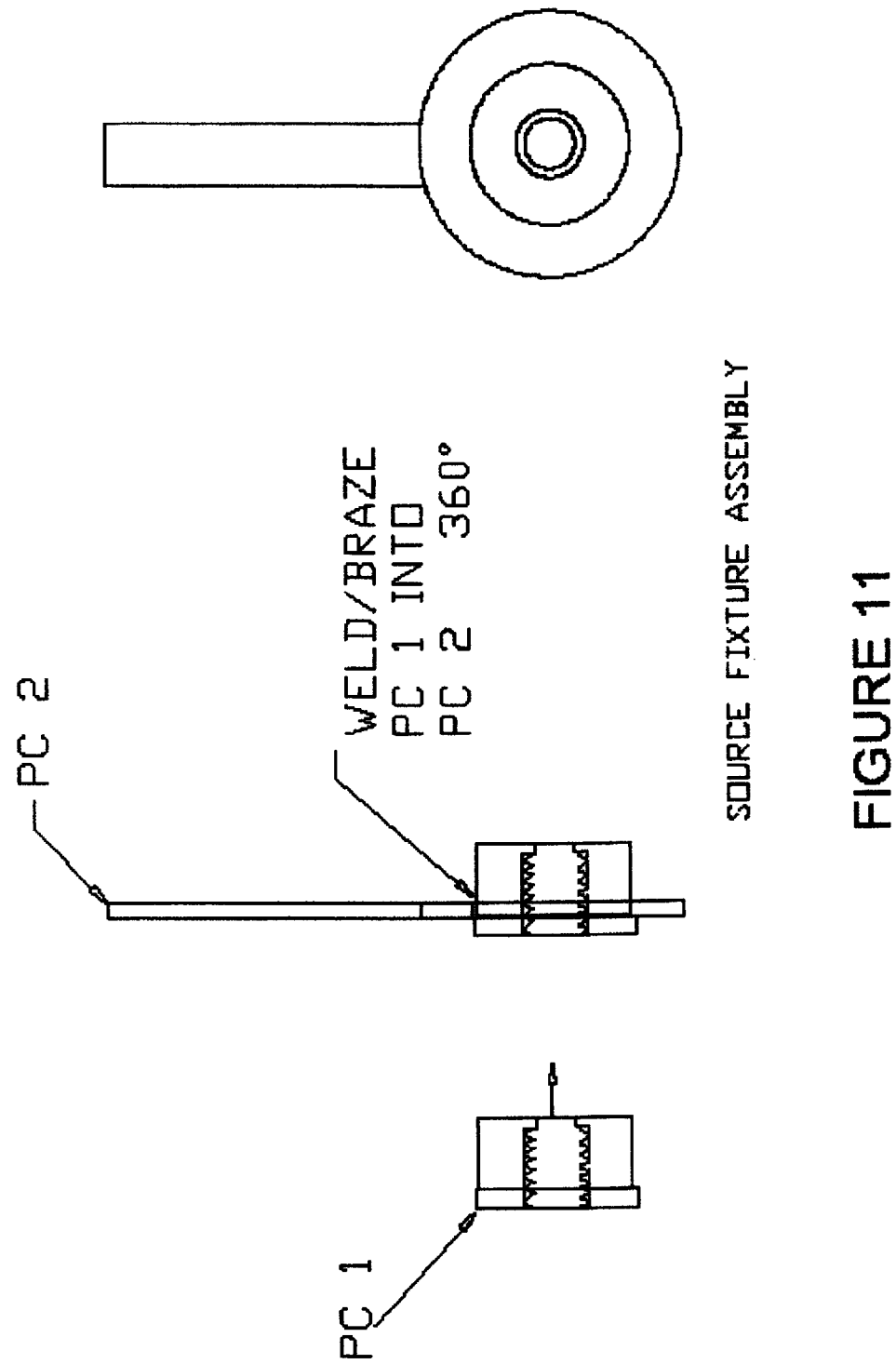
FIG. 11. Source Fixture Assembly.
Figure 12:
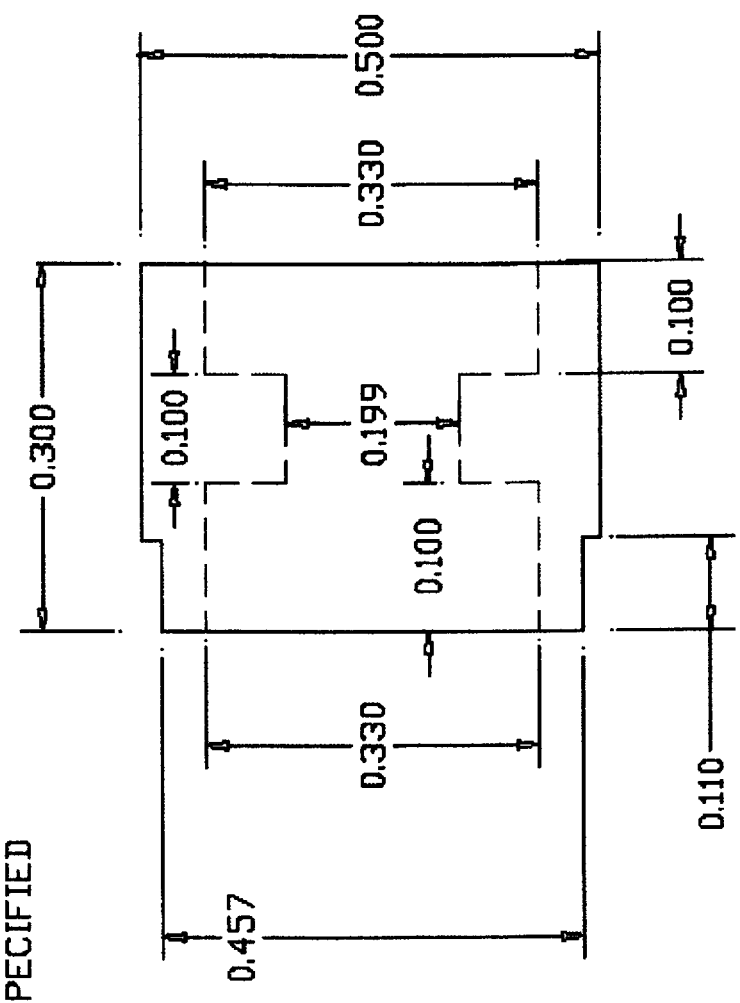
FIG. 12. Source Ceramic Isolator.

FIGS. 11 and 12 show the source fixture assembly and source ceramic isolator which are located in the IMS drift tube shown in FIG. 8. Using an appropriately sized standard hex tool, the source holder is easily installed into the source fixture, after the cell body has been fired. This design and installation procedure is completely unique and allows the manufacture of the ceramic-Kovar® IMS cell without the need to consider the radioactivity at the manufacturing location.

Figure 13:
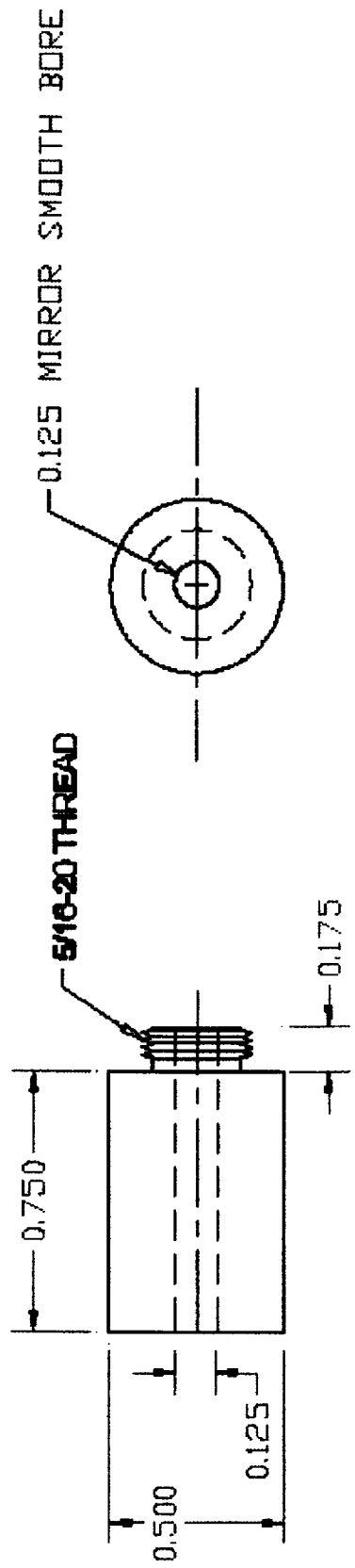
FIG. 13. Explosives Detection Drift Cell Inlet.

Sampling Nozzle Design:

A specially coated gas inlet for the IMS was designed which allows for the very efficient inhalation of certain chemicals (specifically explosive molecules and particles). Explosive molecules are by their nature fragile and heat labile. They are also extremely "sticky", so that a delicate compromise has to be determined balancing gas flow rates and the surface temperatures and composition to which the explosive molecules are subjected. FIG. 13 shows the inlet piece that threads into the end cap of the explosives detection cell as shown in previous figures. This piece is subjected to a proprietary process of Restek Corporation called Silcosteel® treatment which inactivates the stainless steel surface of the inlet piece. Using the thin foil heater previously described, the inlet is normally operated at 150° C. to 180° C. for explosives detection. Without the Silcosteel® treatment much of the explosive material would be catalytically destroyed contacting the surface as the ambient air containing the explosive is inhaled into the instrument. The ID of the inlet piece is only about ⅛ inch which provides a relatively high velocity to the inhaled gas flow, reducing contact of the explosive material on the surface. The inlet piece is contained in a thin tube of the same ZIRCAL-18 refractory board material used to insulate the IMS cell, as discussed previously.

Figure 14A:
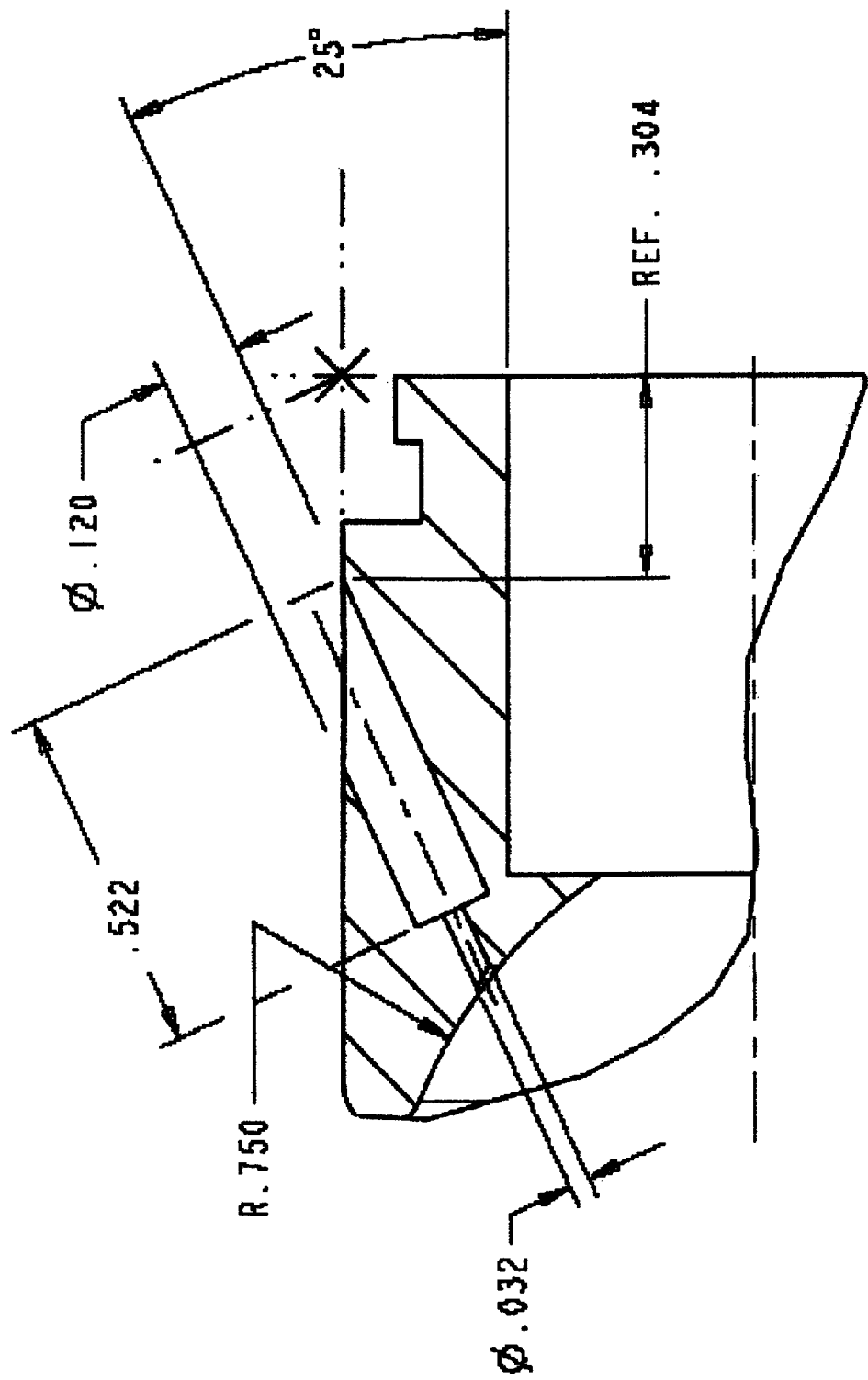
Figure 14B:
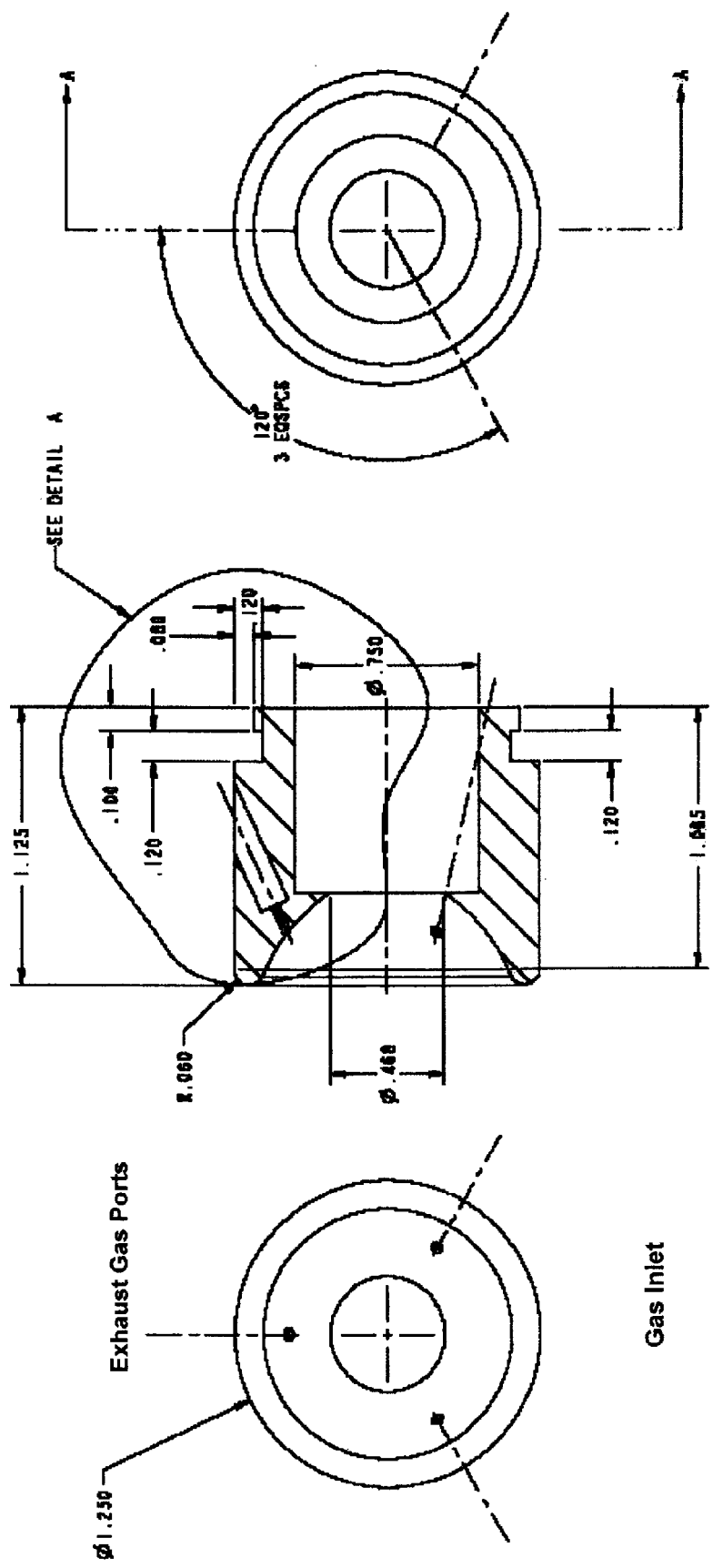

These two pieces together fit into a unique nozzle, the particulars of which are described in FIGS. 14A-14E. This nozzle is made from PEEK™, a relatively inert high temperature plastic. Exhaust gas ports in the nozzle blow gas at the surface to be sampled at carefully determined angles so that explosives can be efficiently sampled from surfaces. As shown in FIG. 14A, the three ports are angled at 25° from the axis of the nozzle. As shown in FIG. 14B, each exhaust gas port is circumferentially disposed at 120° spacings on the interior edge of the nozzle. FIG. 14C is a section view of the nozzle through line A-A as well as a top view along the inlet nozzle axis The directed air flow from the three ports converge approximately 1 inch in front of the nozzle. Material on a surface is efficiently removed at this point via surface perturbation, and directed through the gas inlet nozzle along the longitudinal axis thereof. In addition, the interior surface of the nozzle is slightly concavely curved, which aids in the sample introduction. This inhalation inlet assembly allows trace explosive residues to be effectively introduced into the IMS for measurement. A unique, single pump flow design is employed to both blow air through the nozzle ports, inhale the sampled gas into the IMS inlet, and to provide drift gas flow for the IMS. Typical flow rates are about 800 to 1200 cc/min exhalation flow for the nozzle, 150 cc/min inhalation flow through the inlet piece, and about 50 to 70 cc/min drift flow. A calibrated vent (not shown) is used to make up the difference in flows and allow the pump to work without appreciable back pressure. For the lowest noise contribution, the pump is also controlled using a PWM circuit.

ILLUSTRATIVE EXAMPLE

Gridless IMS Design

Since the inner diameter of the guard rings is only 0.217 inches in the miniaturized design, grid screen structures are not necessary to establish the field uniformly across the area of the ring normal to the ion flow. The ion reservoir is established in the region of the guard ring above the control ring where the voltage potential is the lowest between control pulses.

A prototype of the instant IMS design was operated electrically such that the control function was operated only three guard rings down from the source. This had the effect of increasing the drift length by another three guard rings and reducing the reaction region by the same length. This lengthening of the drift region by approximately 35% should theoretically cause no loss in ion current, since the ions are traveling the same overall distance, but will improve peak resolution. Since the Mini-Cell concept employs the ion reservoir, there is not very much gained by having a very long reaction region. The required reactant ion/sample chemical reactions will occur for the most part in the ion reservoir region.

Figure 15:
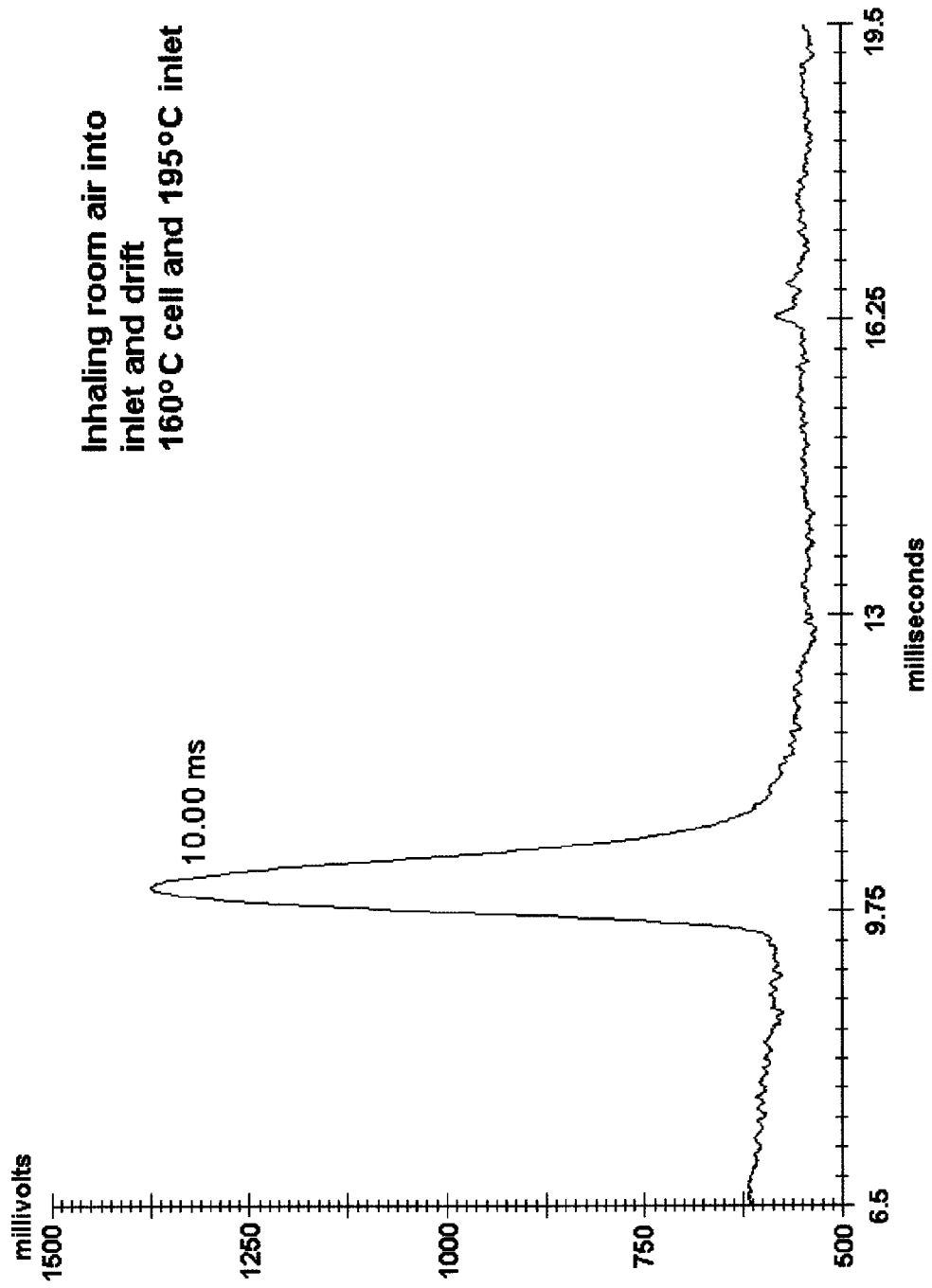
FIG. 15 illustrates a Negative Ion Spectrum.

As can be seen from FIG. 15, a strong well-shaped reactant ion is the only peak evident in the spectrum.

Also, eliminating the screen grid did not negatively affect the performance of the IMS. Actually, since the optical transmission of a grid was only 61%, the actual performance was better, because more ions reached the collector resulting in greater peak amplitude, thus improving signal to noise. Because the ion reservoir technique enabled the IMS to be efficiently miniaturized, the internal diameter became such that the grids were not necessary to establish a uniform field on the radius of the cell. Not using a complicated grid design greatly simplifies the construction of the IMS and also virtually eliminates microphonic noise pickup. The ion injection circuit can be thought of as using a "virtual" grid to control the ion movement.

Figure 16:
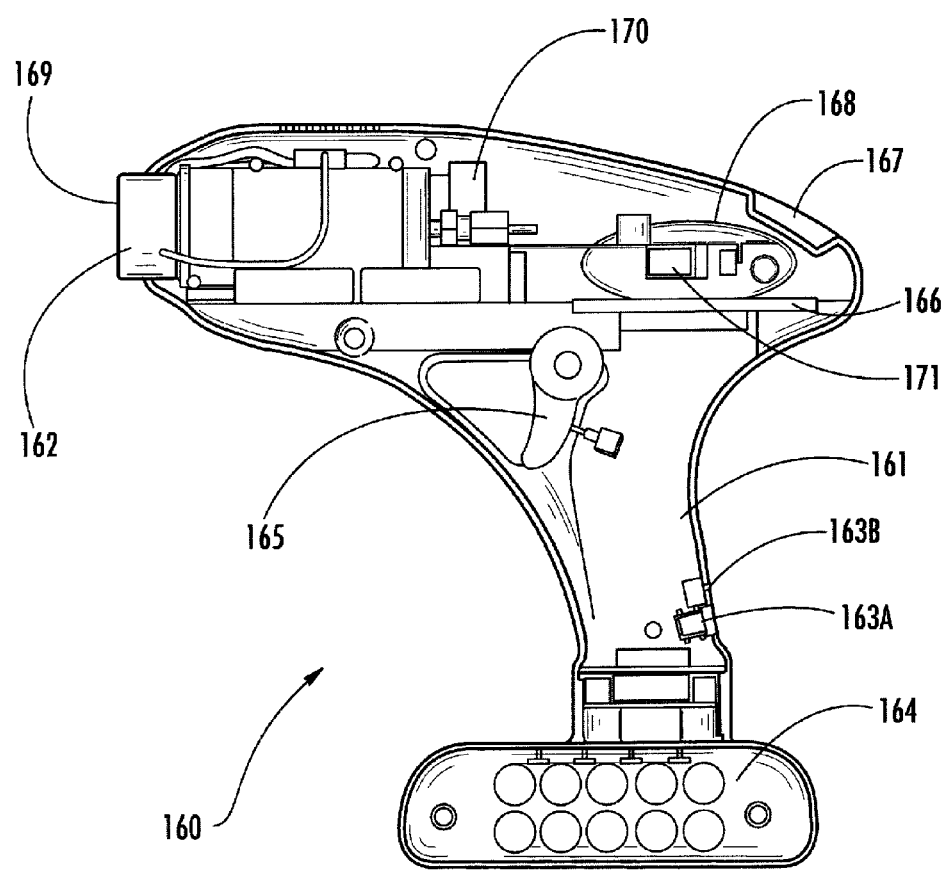
FIG. 16 is a cross-sectional view of a hand-held ion mobility spectrometer.

In accordance with FIG. 16, a handheld ion mobility spectrometer 160 (IMS) for sampling a gaseous stream to detect trace chemicals is shown. The IMS includes a housing 161; a power connector 163A in communication with an on/off switch 163B which may be used to power the unit or alternatively to provide for charging of the on-board battery pack 164; an actuator trigger 165, for sampling initiation; an electrometer 166 for controlling the various processes necessary for operation of the IMS and for calculating results to be forwarded to the LCD viewing screen 167; an ion detection circuit 168; an ion detection assembly detector housing 162, including a sampling nozzle 169 in fluid communication with a gas flow pump, said sampling nozzle 169 including an inhalation inlet and at least one exhaust nozzle port constructed and arranged to facilitate perturbation of a target surface; said gas flow sample pump 170 in fluid communication with said sampling nozzle 169, said gas flow sample pump 170 constructed and arranged to provide exhaust air for flow through said at least one exhaust nozzle port, inhalation flow through said inhalation inlet, and drift gas flow through said IMS; a drift cell construction (not shown, within the detector housing 162) in fluid communication with said sampling nozzle and including therein an ion reservoir in electrical communication with an electronic ion injection control circuit; and an LCD viewing screen 167, or the like, for text display of the output results of the on-board processor; whereby sampling of a gaseous stream is performed and any contaminants contained therein are determined and reported, e.g. via a USB port 171 to a remote PC.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the invention.

What is claimed is:

1. An ion mobility spectrometer (IMS) for sampling a gaseous stream to detect trace chemicals therein comprising:
    a housing;
    a drift cell of hermetic construction, wherein said drift cell comprises a plurality of rings;
    an ion injection control circuit, wherein said ion injection control circuit:
        is programmed to increase a voltage of a ring in order to create no more than one ion reservoir,
        is programmed to decrease a voltage of a ring in order to release ions from the ion reservoir and through a drift tube portion of said drift cell, wherein a magnitude of said voltage increase and decrease is greater than 100V, wherein the voltage increase and decrease is driven by a trigger pulse having a pulse width in a range of 1 to 20 msec, and wherein said voltage increase and decrease is effective to establish an ion reservoir,
        includes a resistive bridge circuit electrically coupled to a high voltage transistor, and
        includes a means for providing a low voltage trigger timing pulse effective for tripping an opto-isolator, wherein said trigger pulse to said opto-isolator causes voltage to the high voltage transistor to vary with said pulse, whereby said transistor provides a sharp square wave voltage pulse to a ring effective to produce said voltage decrease which causes ions in the ion reservoir to be injected into the drift tube portion of the drift cell;
    an electrometer;
    an ion detection circuit having signal processing, spectra generation and manipulation and digital readout capability;
    an ion generation and detection assembly, including therein an ionization source and ion reservoir in electrical communication with an electronic ion injection control circuit; and
    a viewing screen;
    whereby sampling of a gaseous stream is performed and any contaminants contained therein are determined and reported and whereby said ionization source is 20 microcuries or less.

2. The ion mobility spectrometer of claim 1, wherein said ion detection assembly includes a sampling nozzle including an inhalation inlet and at least one exhaust nozzle port constructed and arranged to facilitate perturbation of a target surface; a gas flow sample pump in fluid communication with said sampling nozzle, said gas flow sample pump constructed and arranged to provide exhaust air for flow through said at least one exhaust nozzle port, inhalation flow through said inhalation inlet, and drift gas flow through said IMS, and wherein said sampling nozzle includes a central inhalation port and a plurality of circumferentially disposed exhalation ports, said exhalation ports constructed and arranged to have a common intersection point for enhanced perturbation of a target surface;
    whereby material perturbed from said target surface is inhaled into said IMS.

3. The ion mobility spectrometer of claim 1, wherein said drift cell construction includes:
    a hermetically sealed drift tube construction using ceramic insulating rings joined to metal rings formed from a nickel-cobalt ferrous alloy by an active metal joining process, thereby providing a self-enclosed cell construction;
    said metal rings being constructed and arranged to be electrically coupled to a high voltage control and electrometer board, whereby said hermetically sealed drift tube prevents outside contaminants from being introduced therein;
    whereby analysis of ultra high purity gases is enabled.

4. The ion mobility spectrometer of claim 3 wherein said drift tube enables elimination of any screen grids.

5. The ion mobility spectrometer of claim 3 further including:
    a thin foil heater constructed and arranged to wrap around and heat the cell.

6. The ion mobility spectrometer of claim 5, further including an insulating member constructed and arranged to encase the cell and heater.

7. The ion mobility spectrometer of claim 6, further including a protective housing constructed and arranged to enclose the insulating member encased cell and heater and provide electro-magnetic-force (EMF) shielding.

8. The ion mobility spectrometer of claim 5, wherein said thin foil heater has two separate heater zones which allow the drift cell body and gas inlet to be independently heated.

9. The ion mobility spectrometer of claim 5, wherein said heater is controlled using a pulse-width-modulated voltage supply.

10. The ion mobility spectrometer of claim 3, wherein a radioactive source holder is provided for threadable engagement with a source fixture assembly, thereby enabling manufacture of the IMS drift cell absent any presence of radioactive material therein.

11. The ion mobility spectrometer of claim 1 wherein said electronic ion injection control circuit provides a sufficiently high voltage to achieve a uniform control voltage radially across the ion drift tube diameter thereby enabling elimination of any ion control grids.

12. An ion mobility spectrometer for sampling a gaseous stream to detect trace chemicals therein comprising:
a housing;
a drift cell having a diameter and comprising a plurality of rings;
an ion injection control circuit, wherein said ion injection control circuit:
is programmed to increase a voltage of a ring in order to create no more than one ion reservoir,
is programmed to decrease a voltage of a ring in order to release ions from the ion reservoir and through a drift tube portion of said drift cell, wherein a magnitude of said voltage increase and decrease is greater than 100V and wherein the voltage increase and decrease is driven by a trigger pulse having a pulse width in a range of 1 to 20 msec, and wherein said voltage increase and decrease is effective to establish an ion reservoir,
includes a resistive bridge circuit electrically coupled to a high voltage transistor, and
includes a means for providing a low voltage trigger timing pulse effective for tripping an opto-isolator, wherein said trigger pulse to said opto-isolator causes voltage to the high voltage transistor to vary with said pulse, whereby said transistor provides a sharp square wave voltage pulse to a ring effective to produce said voltage decrease which causes ions in the ion reservoir to be injected into the drift tube portion of the drift cell;
an electrometer;
an ion detection circuit having signal processing, spectra generation and manipulation and digital readout capability;
an ionization source wherein said ionization source is 20 microcuries or less.

13. The ion mobility spectrometer of claim 12 wherein said ionization source is contained in a source holder and wherein said source holder is detachably connected to said drift tube.

14. The ion mobility spectrometer of claim 12, further comprising an ion detection assembly, wherein said ion detection assembly includes a sampling nozzle; a gas flow sample pump in fluid communication with said sampling nozzle, said gas flow sample pump arranged to provide air through a plurality of exhaust nozzle ports, wherein said sampling nozzle includes a central inhalation port and wherein said plurality of exhaust nozzle ports are circumferentially disposed around said central inhalation port and arranged to be directed toward the same target surface point to enhance perturbation of the target surface, whereby material perturbed from said target surface is inhaled into the ion mobility spectrometer.

15. The ion mobility spectrometer of claim 12, wherein said drift tube is a hermetically sealed drift tube having ceramic insulating rings joined to metal rings, thereby providing a self-enclosed cell construction.

16. The ion mobility spectrometer of claim 15, wherein said metal rings are electrically coupled to a high voltage control and electrometer board, wherein said hermetically sealed drift tube prevents outside contaminants from being introduced therein.

17. The ion mobility spectrometer of claim 12 wherein said electronic ion injection control circuit selectively provides a voltage radially across the drift tube diameter and wherein said selective voltage controls ion movement into the drift region.

18. The ion mobility spectrometer of claim 12 wherein said electronic ion injection control circuit selectively provides a voltage radially across the drift tube diameter and wherein said selective voltage controls an accumulation of ions in the drift region.

19. The ion mobility spectrometer of claim 18 wherein said ion accumulation in the drift region is controlled without using a physical grid.

20. The ion mobility spectrometer of claim 12, wherein a source holder arranged to hold the ionization source engages with a source fixture assembly.

21. The ion mobility spectrometer of claim 12 further including a thin foil heater constructed and arranged to wrap around and heat the drift tube.

22. The ion mobility spectrometer of claim 21, further including an insulating member constructed and arranged to encase the tube and heater.

23. The ion mobility spectrometer of claim 22, further including a protective housing constructed and arranged to enclose the insulating member encased tube and heater and provide electro-magnetic-force (EMF) shielding.

* * * * *